(12) United States Patent
Yang

(10) Patent No.: US 7,410,478 B2
(45) Date of Patent: *Aug. 12, 2008

(54) SAFETY SYRINGE WITH NEEDLE RETRACTING MECHANISM

(75) Inventor: Chung-Yu Yang, Taipei (TW)

(73) Assignees: Chih Ming Wang, Keelung (TW); Hsi-Hsun Tseng, Keelung (TW); Po-Liang Lee, Keelung (TW); Chun-Chieh Chuang, Keelung (TW)

( * ) Notice: Subject to any disclaimer, the term of this patent is extended or adjusted under 35 U.S.C. 154(b) by 694 days.

This patent is subject to a terminal disclaimer.

(21) Appl. No.: 10/749,563

(22) Filed: Jan. 2, 2004

(65) Prior Publication Data

US 2004/0143215 A1 Jul. 22, 2004

Related U.S. Application Data

(63) Continuation-in-part of application No. 10/347,800, filed on Jan. 22, 2003, now Pat. No. 7,074,207, which is a continuation-in-part of application No. 09/931,014, filed on Aug. 17, 2001, now abandoned.

(51) Int. Cl.
*A61M 5/00* (2006.01)

(52) U.S. Cl. ..................... 604/110; 604/195

(58) Field of Classification Search ................ 604/110, 604/111, 187, 198, 195, 218, 260, 181, 263
See application file for complete search history.

(56) References Cited

U.S. PATENT DOCUMENTS

| 4,828,548 | A | | 5/1989 | Walter | 604/164 |
| 5,114,410 | A | | 5/1992 | Caralt Batlle | 604/195 |
| 5,997,512 | A | * | 12/1999 | Shaw | 604/195 |
| 7,074,207 | B2 | * | 7/2006 | Yang | 604/110 |

FOREIGN PATENT DOCUMENTS

WO    WO 95/31236 A1    11/1995

* cited by examiner

*Primary Examiner*—Nicholas D. Lucchesi
*Assistant Examiner*—Christopher D Koharski
(74) *Attorney, Agent, or Firm*—Bacon & Thomas PLLC

(57) ABSTRACT

A safety syringe includes a flexible holder-supporting seat that is sleeved around and that clamps a needle holder within a front end portion of a syringe barrel. A flexible sealing member seals an open front end of a plunger so as to define a vacuuming chamber in the plunger. When the plunger moves within the barrel to a front limit position, a holder-retaining front portion of the sealing member engages and retains the needle holder thereon. The plunger pushes the holder-supporting seat to separate from the needle holder such that the sealing member and the needle holder mover rearward within the syringe barrel due to negative pressure produced in the plunger, thereby retracting a needle into the syringe barrel.

17 Claims, 31 Drawing Sheets

SAFETY SYRINGE WITH NEEDLE RETRACTING MECHANISM

This application is a continuation-in-part application of pending U.S. application Ser. No. 10/347,800, filed Jan. 22, 2003 now U.S. Pat No. 7,074,207, which is a continuation-in-part of Ser. No. 09/931,014, filed Aug. 17, 2001, now abandoned.

BACKGROUND OF THE INVENTION

1. Field of the Invention

The present invention relates to a medical syringe, and more particularly to a safety syringe with an automatically retractable needle.

2. Description of the Prior Art

As shown in FIG. 1, a prior syringe includes a syringe barrel 72 with a hole in the front end of the syringe barrel 72 and scales on the surface of the syringe barrel 72. A needle unit 73 includes needle holder 730 with the thread of a screw for bolting the needle unit 73 in the syringe barrel 72. The rear end of the needle 731 is fastened across the needle holder 730, wherein the front end of the needle 731 is projected from the needle holder 730. The rear end of the syringe barrel 72 includes a rear opening 724 with large cross-sectional area or the diameter. A rubber-sealing ring 743 fastens a rod 74 inside the syringe barrel 72, wherein the rod 74 is movable across the rear opening 724. The external diameter of the rubber-sealing ring 743 is slightly larger than the internal diameter of the rear opening 724 and the internal diameter of the syringe barrel 72. The rubber-sealing ring 743 injects the medicament withdrawn inside the syringe barrel 72 through the needle 731 when the rod 74 is pushed.

The needle 731 may accidentally stab an operating staff while the operating staff encloses the needle 731 by a needle sheath. If the syringe 7 is used and the needle 731 comes in contact with the blood of an individual, the stabbed operating staff may become infected with diseases, e.g. AIDS, viral hepatitis b and so on.

The medical appliances are improved to protect operating staff from being inflected. Safety syringes protect the operating staff from being stabbed and infected while tidying the needle 731 after injecting the medicament for patients. As shown in FIGS. 2A and 2B, a safety syringe 8, which is disclosed by U.S. Pat. No. 5,395,337, includes a syringe barrel 82 and a spring 84. The syringe barrel 82 includes a tapered wall 824 for fastening a needle holder 830. A flexible sealing member 85 is wedged in the front end of the spring 84 by a retaining ring 850 having a lead angle. A spring 86 connects with the flexible sealing member 85 to pull the flexible sealing member 85 when the operating staff finishes the injection. As shown in FIG. 2B, the operating staff can tidy the needle 831 by pushing the spring 84 to wedge the flexible sealing member 85 by the tapered wall 824. When the tapered wall 824 wedges the flexible-sealing member 85, the flexible sealing member 85 is released from the retaining ring 850 if the operating staff continuously pushes the spring 84. The flexible sealing member 85 is pulled by the spring 86 to movably dispose inside the spring 84 after the flexible-sealing member 85 is released from the retaining ring 850.

However, the diameter of the tapered wall 824 of a syringe is very small, e.g. few millimeters, wherein the capacity of the syringe is approximately 1 cubic centimeter or 2 cubic centimeters. It is pretty difficult to push the tapered wall 824 while wedging the flexible-sealing member 85 by the tapered wall 824 without partiality. It is also difficult to set the spring 86 in the spring 84 to connect the flexible sealing member 85 with the rear end of the spring 84 of a tiny syringe 7. The complex and delicate process for fabricating elements of the tiny syringe 7 increases the cost of the tiny syringe 7. The syringe 7 may be too expensive for selling. Thus it is necessary to develop more economical safety syringes for protecting the operating staff from being stabbed.

SUMMARY OF THE INVENTION

In accordance with the present invention, a safety syringe is provided to substantially overcome the drawbacks of the above mentioned problems for automatically retracting the needle unit inside a plunger by pressure.

Accordingly, it is another objective of the present invention to provide a safety syringe, which can be conveniently operated, with convenient fabricated elements for protecting the operating staff from being stabbed and infectious diseases.

In accordance with the present invention, a safety syringe is disclosed. The present safety syringe includes a syringe barrel, a flexible holder-supporting seat, a needle unit, a plunger and a flexible sealing member. The syringe barrel includes a barrel body with a front opening and a rear opening, wherein the cross-sectional area or the diameter of the rear opening is larger than the front opening. A spacer portion is disposed in the front end of the barrel body, wherein the front opening penetrates the spacer portion. The flexible holder-supporting seat is sleeved around and clamps a needle holder of the needle unit within the front-end portion of a syringe barrel, wherein the flexible holder-supporting seat includes a through hole. The needle unit includes the needle holder and a needle fastened on the needle holder, wherein the needle includes a rear opening. The needle unit is inserted into the front end of the syringe barrel. The needle holder is propped by a spacer portion. The needle inserts through the spacer portion and is projected from the front opening. The plunger includes a front-end wall, a rear end wall and a plunger body formed between the front-end wall and the rear end wall. The cross-sectional area or the diameter of a front opening of the plunger is larger than the external diameter of the spacer portion. An inward flange is formed in the front portion of the plunger. The plunger is disposed inside the syringe barrel and is movable between the flexible holder-supporting seat and the rear opening. The sealing member is disposed continuously within the inward flange to seal the front opening formed in the front of the plunger for defining a sealed space with lower pressure. The sealing member combines with the needle unit when the front end of the plunger is pushed to be close to the holder-supporting seat. The plunger pushes the holder-supporting seat to release the needle holder combined with the sealing member. The needle holder is propped by the spacer portion to stop the movement of the sealing member, so the sealing member is released from the inward flange while the sealing member being not contacted by the inward flange. Thus the sealing member and the needle unit is automatically retracted into the plunger body due to negative pressure.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
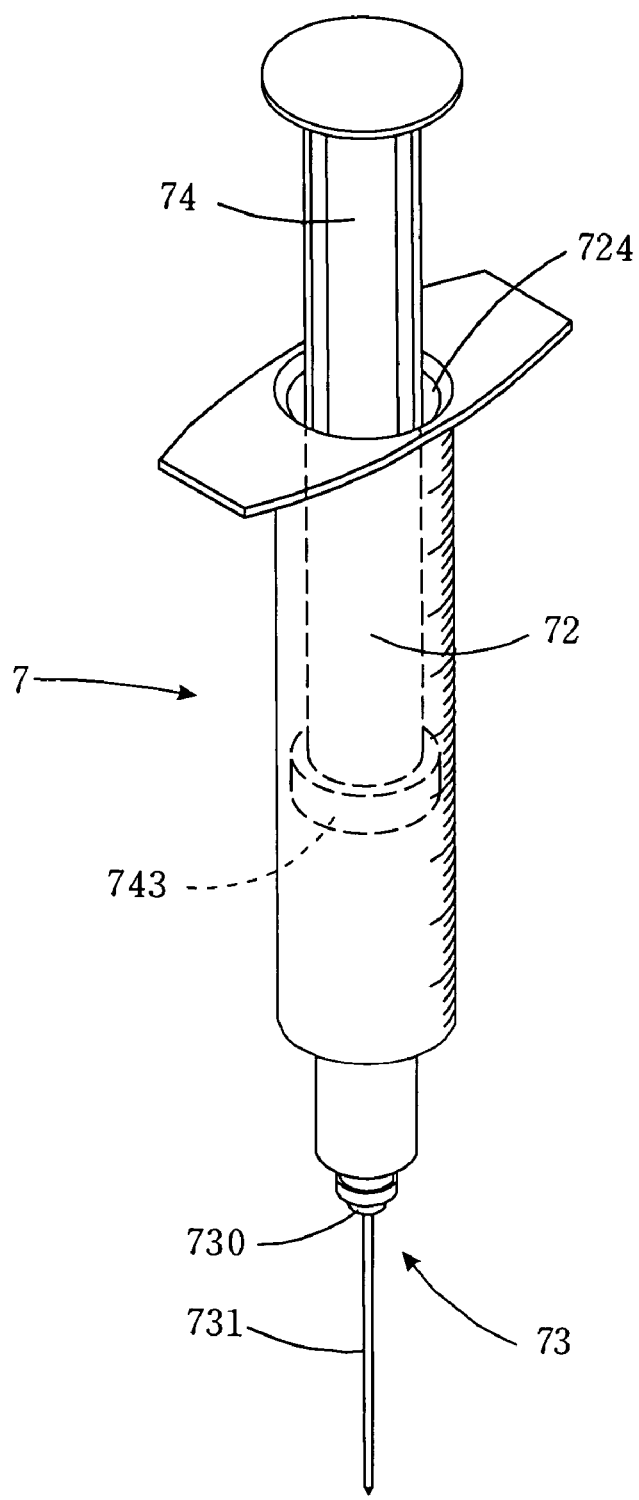
FIG. 1 illustrates a schematic diagram of a safety syringe in the prior art
Figure 2A:
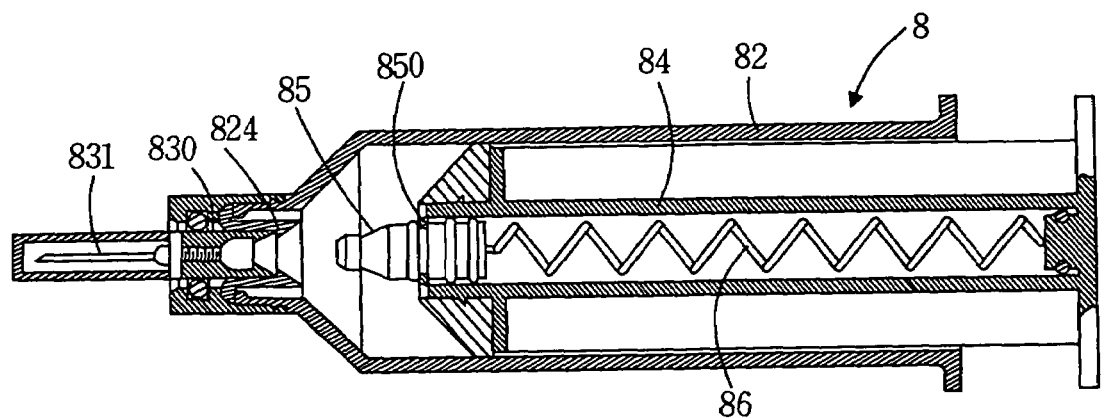
FIG. 2A illustrates a longitudinal cross-sectional view of a safety syringe incorporating the plunger in the prior.
Figure 2B:
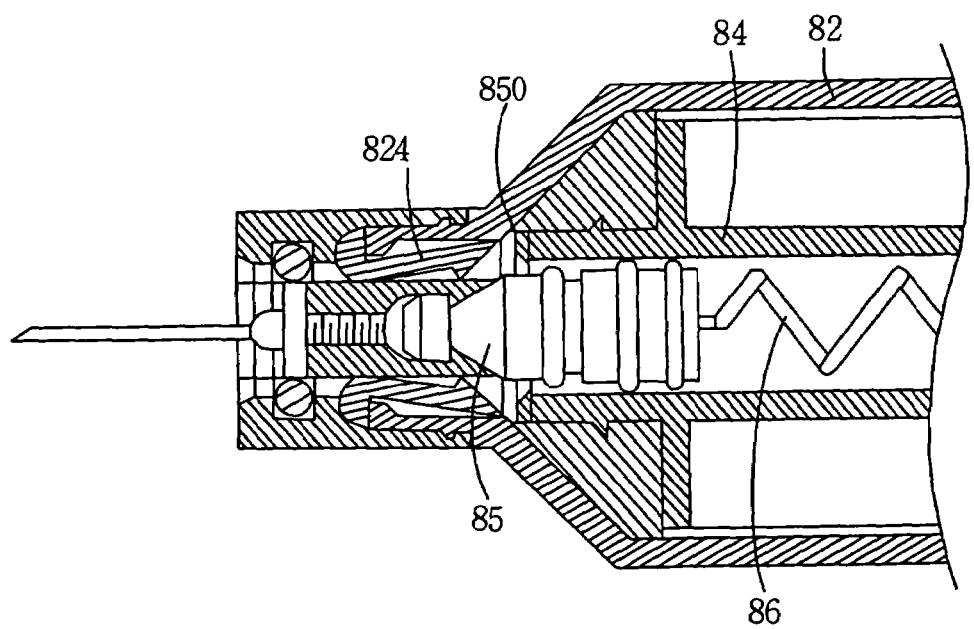
FIG. 2B illustrates a view similar to FIG. 2A, showing final movement of the safety syringe in the prior art

These preferred embodiments of the present invention are now described in greater detail. Nevertheless, it should be recognized that the present invention can be practiced in a wide range of other embodiments besides those explicitly described, and the scope of the present invention is expressly not limited except as specified in the accompanying claims.

As shown in FIGS. 3A-3D, the first embodiment of the present invention provides a safety syringe including a syringe barrel 2, a needle unit 3 set in the front end of the syringe barrel 2, a plunger 4 movably disposed within the syringe barrel 2 and a flexible sealing member 5 disposed movably within the front end of the plunger 4.

The syringe barrel 2 includes a barrel body 20, a front-end wall 21 and a rear end wall 22. A front opening 210 and the front-end wall 21 are integrally formed. A rear opening 220 is formed integrally with the rear end wall 22. The cross-sectional area of the rear opening 220 is slightly larger than the cross-sectional area of the plunger 4; thus the plunger 4 can be inserted into the syringe barrel 2. A spacer portion 212 is disposed on the front end wall 21, wherein the front opening 210 penetrates the spacer portion 212. The spacer portion 212 and the barrel body 20 can be formed integrally. However, the spacer portion 212 may be an independent element set on the front end of the barrel body 20. The cross-sectional area or the diameter of the front opening 2 10 is slightly smaller than that of the rear opening 220 and the plunger 4. The internal diameter of the syringe barrel 2 and the internal diameter of the rear opening 220 are approximately the same. A flexible holder-supporting seat 24 including a central hole 240 can be pushed into the syringe barrel 2 through the rear opening 220 to be set inside the syringe barrel 2. There is a distance between the flexible holder-supporting seat 24 and the front-end wall 21 of the barrel body 20.

A needle unit 3 includes a needle body 30 and a needle 31 set across the needle body 30. The needle body 30 is movably set inside the flexible holder-supporting seat 24. The front end of the needle 31 is set across the spacer portion 212 to pierce through the spacer portion 212.

The plunger 4 includes a plunger body 40 including an open front end 41 formed on an end of plunger body 40. The open front end 41 includes a front opening 410, wherein the internal diameter of the front opening 410 is slightly larger than the cross-sectional area or the diameter of the needle body 30. A flexible sealing member 5 is fastened inside the front opening 410 to form a sealed space inside the plunger body 40. A rear end wall 45 is fastened on another end of plunger body 40 to form the sealed space inside the plunger body 40. The plunger 4 fastened inside the barrel body 20 can be moved away from the syringe barrel 2 by pulling the rear end wall 45 to withdraw the medicament. The plunger 4 can be pushed to inject the medicament by pushing the rear end wall 45. The plunger body 40 may include a rubber seal ring 43 to fasten the syringe barrel 2 and the plunger 4 better for preventing the medicament inside syringe barrel 2 from overflowing.

Figure 3A:
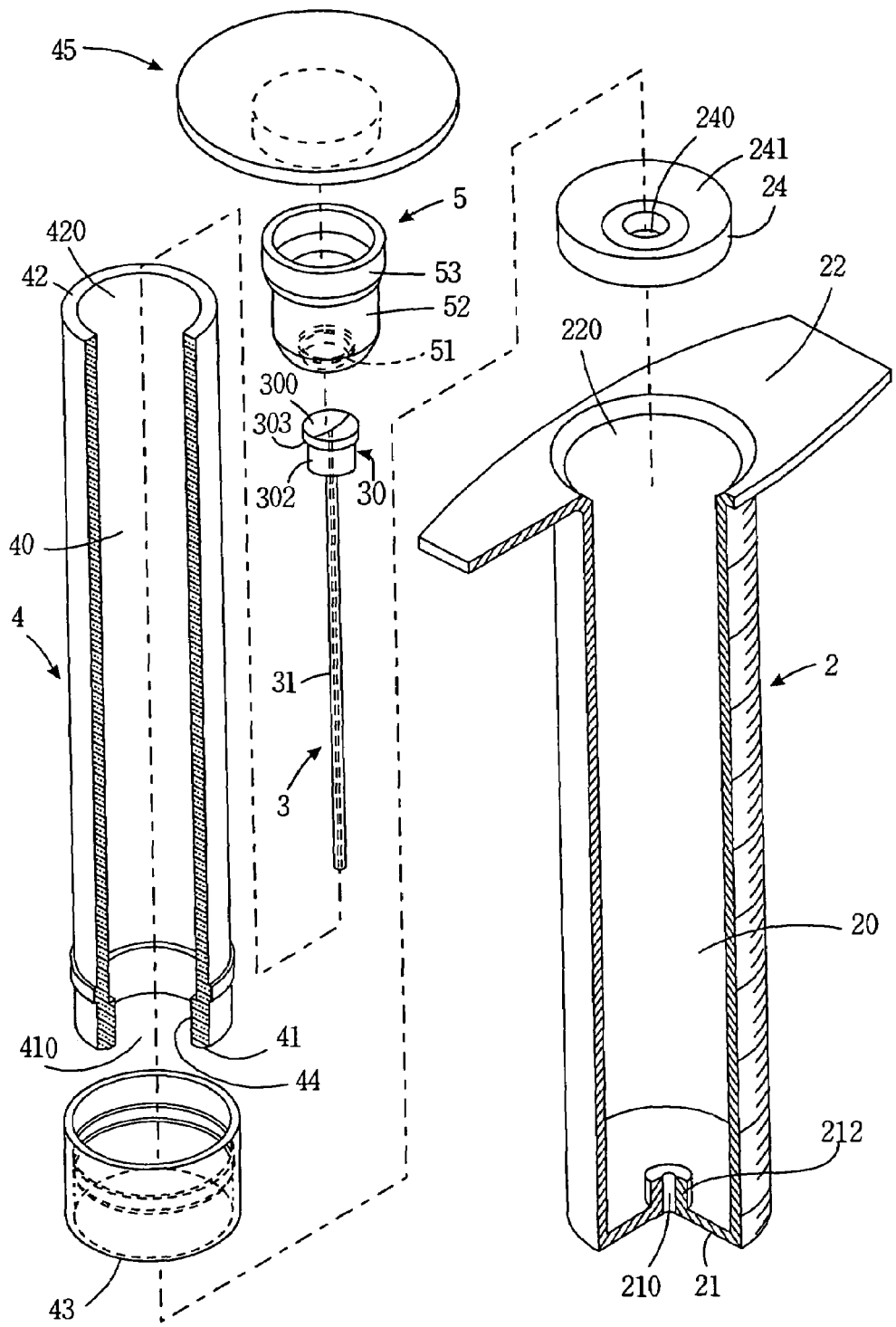
FIGS. 3A-3G illustrate sectional views of a safety syringe of the first embodiment of the present invention.
Figure 3B:
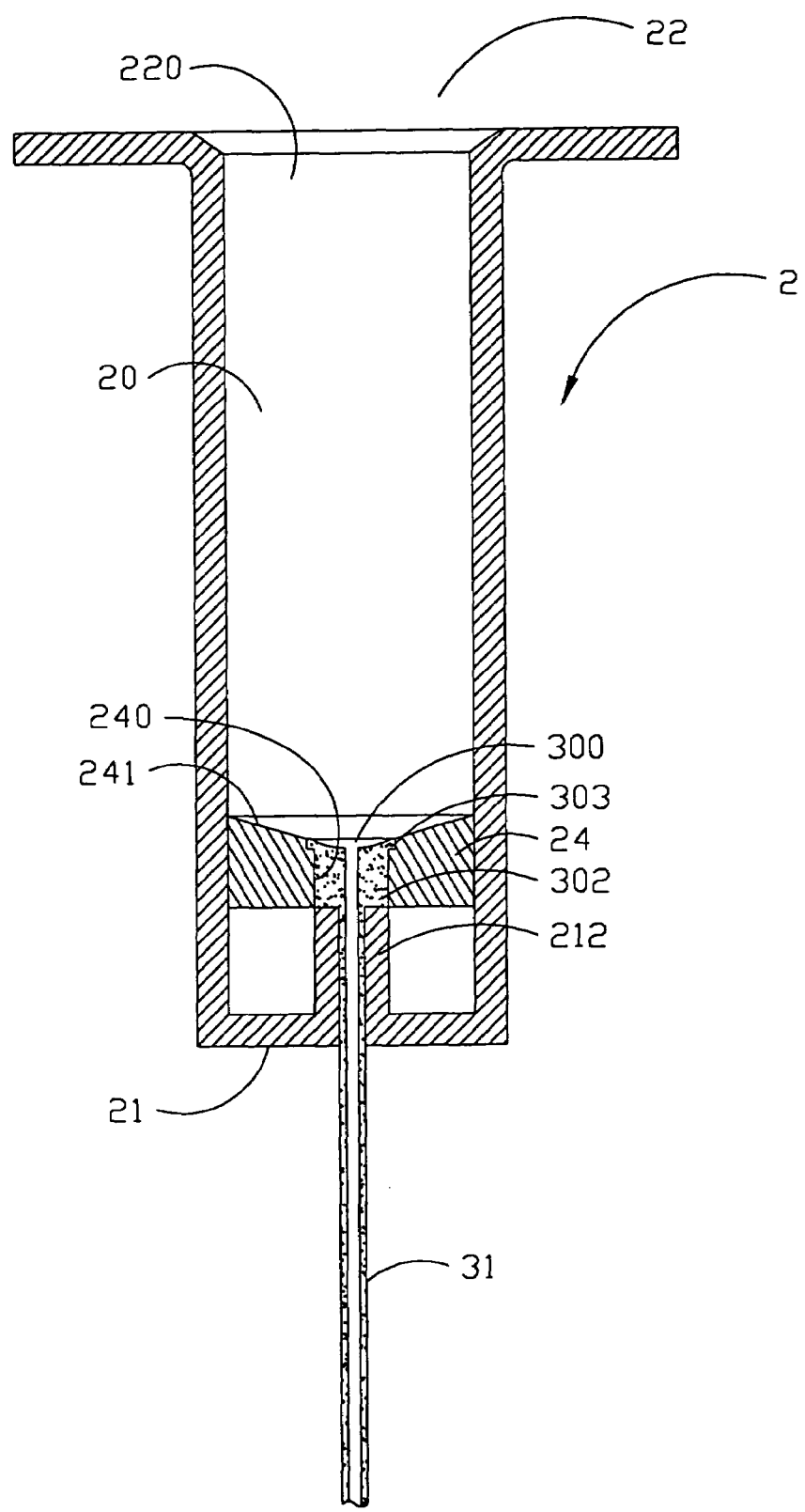

As shown in FIG. 3B, the flexible holder-supporting seat 24 is set inside the syringe barrel 2 to fasten the needle body 30 on. The needle body 30 includes a needle holder 302, a rear opening 300 and an outward flange 303, wherein the cross-sectional area or the diameter of the outward flange 303 is slightly larger than that of the needle holder 302. The cross-sectional area or the diameter of the needle holder 302 may be equal to or slightly larger than that of the spacer portion 212. The flexible holder-supporting seat 24 includes a rear end surface 241. The side of the central hole 240 of the flexible holder-supporting seat 24 fastens the needle holder 302 when the needle body 30 is stuffed into the flexible holder-supporting seat 24. The side of the central hole 240 also fastens the outward flange 303. After the needle body 30 is fastened by the flexible holder-supporting seat 24, the needle body 30 and the flexible holder-supporting seat 24 can be pushed into the syringe barrel 2 through the rear opening 220 until the needle holder 302 contacting with the spacer portion 212. The needle unit 3 set on the front end of the syringe barrel 2 is fastened well and stable because the area of the needle holder 302 contacting with the spacer portion 212 is large enough to provide enough force of stability. When the volume of the medicament withdrawn inside the syringe barrel 2 is approximately 1 cubic centimeter or 2 cubic centimeters, the layout of the prevent invention provides effective stability of the safety syringe for fastening the needle unit 3 and the syringe barrel 2.

Figure 3C:
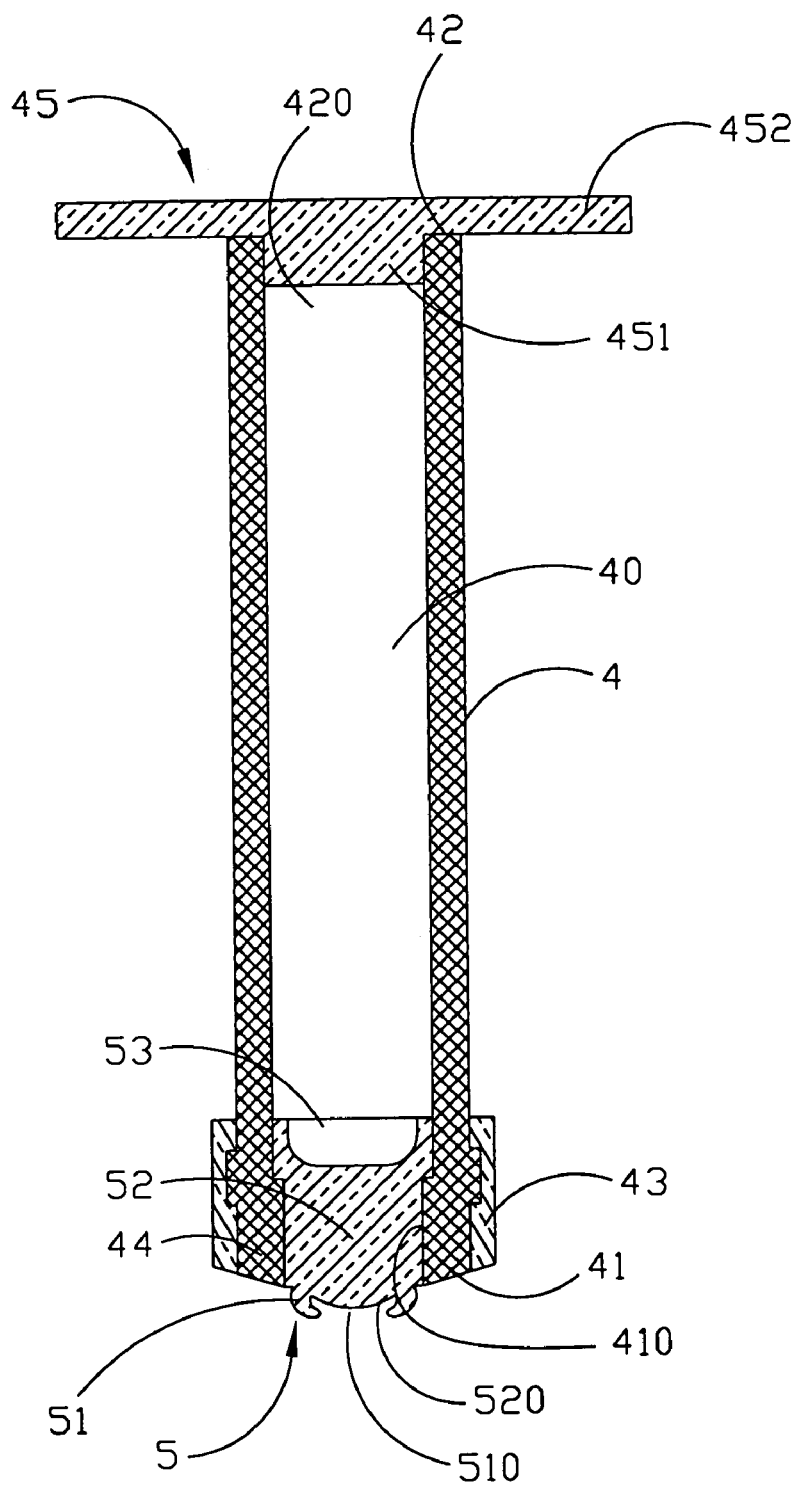

As shown in FIG. 3C, an inward flange 44 of the plunger 4 fastens the flexible sealing member 5. A rear opening 420 and the open rear end 42 are formed integrally. The plunger 4 further comprises a rear end wall 45 sealing the rear opening 420. The rear end wall 45 includes a plate 452 and a circular projection 451 extended from the plate 452. The circular projection 451 is fastened inside the plunger body 40 of the plunger 4, wherein the external diameter of the circular projection 451 is a slightly larger than the internal diameter of the rear opening 420 of the plunger 4. The flexible sealing member 5 includes a sealing rear portion 52 and a holder-retaining front portion 51 extended from the front end of the sealing rear portion 52. The flexible sealing member 5 further includes a rear end skirt portion 53 in the rear end of the flexible sealing member 5. The external diameter of the sealing rear portion 52 is slightly smaller than the internal diameter of the rear opening 420, the sealing rear portion 52 can be pushed into the rear opening 420 of the plunger body 40 thus. The external diameter of the sealing rear portion 52 is slightly larger than the internal diameter of the inward flange 44 of the plunger 4. The flexible sealing member 5 can be fastened on the open front end 41 by fastening to the inward flange 44 to seal the space inside the plunger 4. Thus, the air inside the plunger body 40 is pumped out to form a sealed space with lower pressure inside the plunger body 40, and then the rear end wall 45 is fastened on the rear opening 420 to seal the sealed space. A rubber seal ring 43 is covered on the front end of the plunger 4, wherein the external diameter of the rubber seal ring 43 is slightly larger than the internal diameter of the barrel body 20.

Figure 3D:
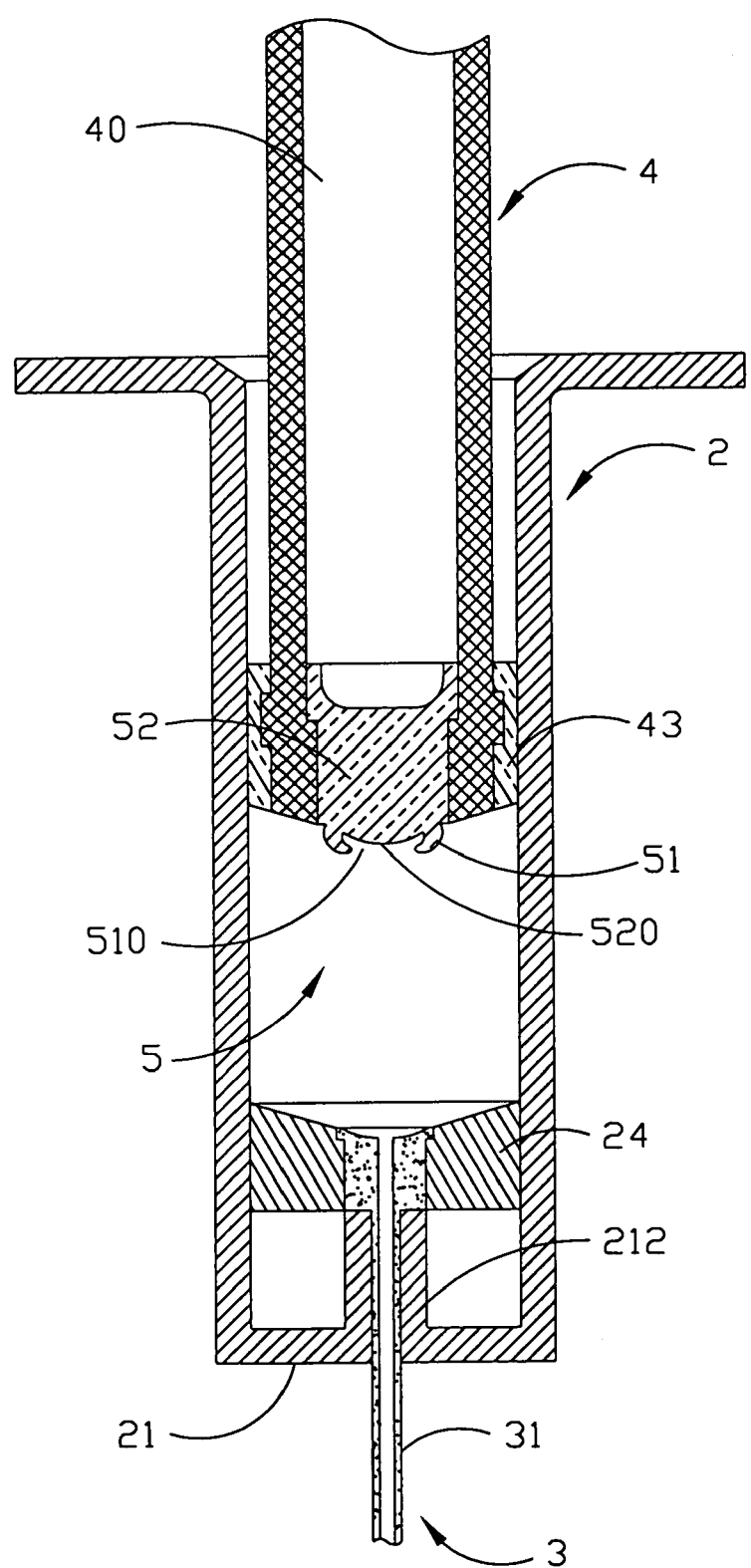
Figure 3E:
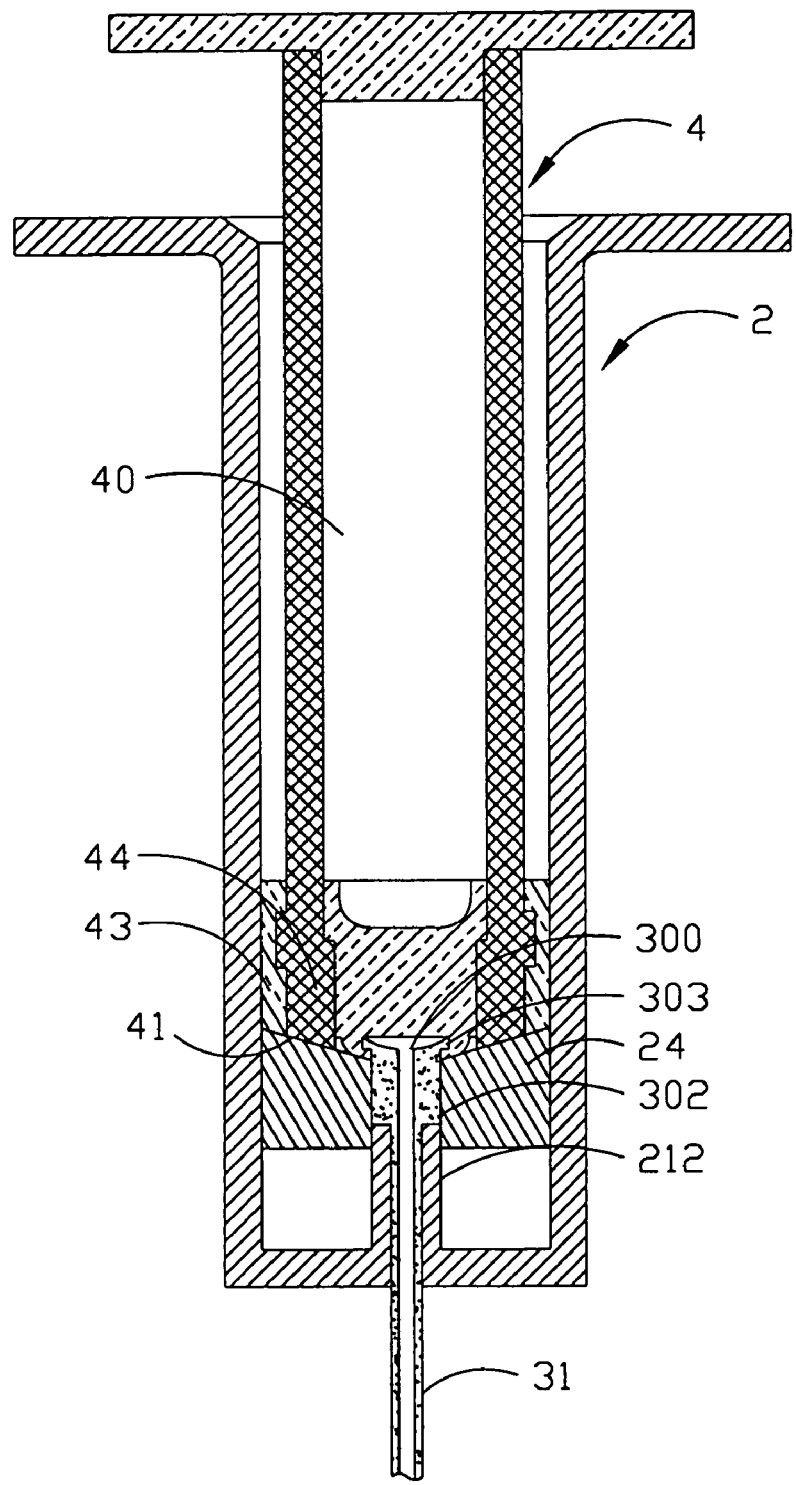

The cannular holder-retaining front portion 51 of the flexible sealing member 5 is extended forward from the sealing rear portion 52, and the external diameter of the holder-retaining front portion 51 is as small as the forward extension. A blind hole 510 is formed inside the holder-retaining front portion 51, wherein the bottom of the blind hole 510 is a sealing rear portion 520, and the top of the blind hole 510 is surrounded by the front end of the holder-retaining front portion 51. The internal diameter of the front end of the holder-retaining front portion 51 is slightly smaller than the external diameter of the outward flange 303. As shown in FIG. 3D, the plunger 4 is set inside the syringe barrel 2. As shown in FIG. 3E, the blind hole 510 sleeves around the outward flange 303. The sealing rear portion 520 seals the rear opening 300 of the needle body 30 to stop the medicament from being injected, when the open front end 41 is pushed to contact with the flexible holder-supporting seat 24. When the open front end 41 is pushed continuously, the needle holder 302 is fastened on the spacer portion 212 but the open front end 41 continuously pushes the flexible holder-supporting seat 24. The flexible holder-supporting seat 24 does not fasten the needle body 30, if the flexible holder-supporting seat 24 is pushed continuously by the open front end 41.

Figure 3F:
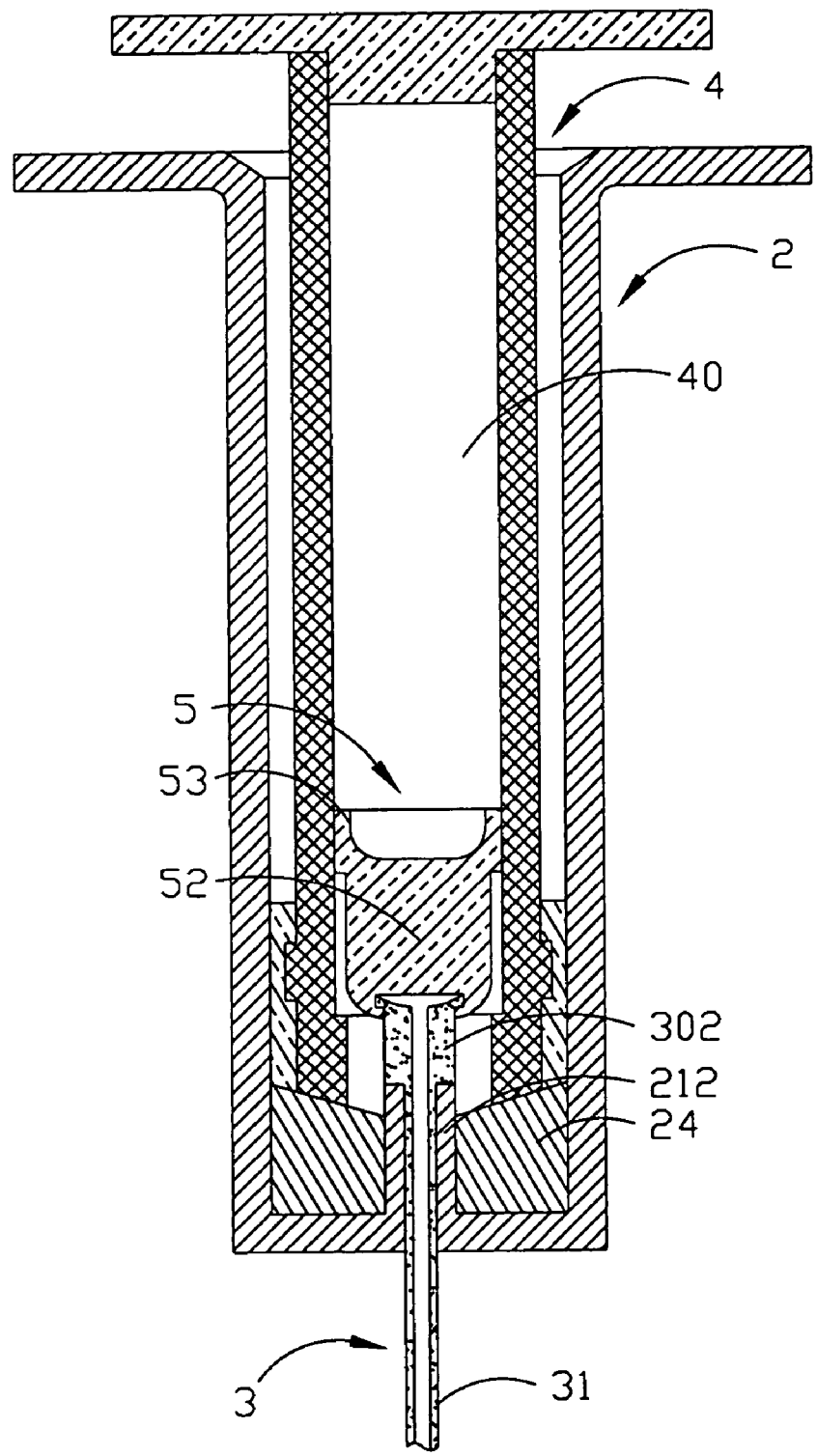
Figure 3G:
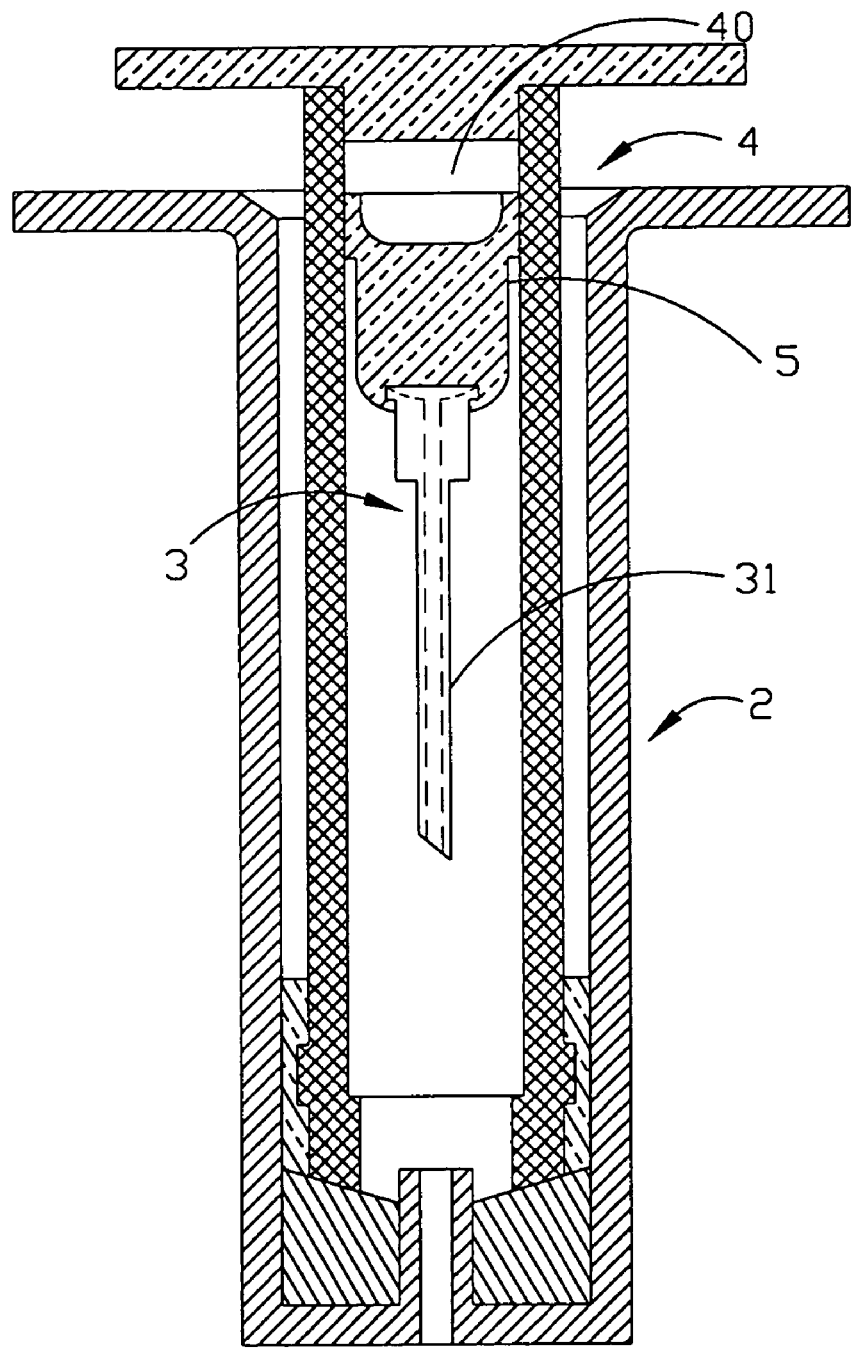

As shown in FIG. 3F, the flexible sealing member 5 stops moving because the needle body 30 props the flexible sealing member 5 up, even if the open front end 41 continuously pushes the flexible holder-supporting seat 24. The flexible sealing member 5 is released from the inward flange 44 when the inward flange 44 does not contact with the flexible sealing member 5. The pressure inside the space sealed by the sealing rear portion 52 and the plunger body 40 is lower than the pressure pulling the sealing rear portion 52. As shown in FIG. 3G, the needle unit 3 that is combined with the flexible sealing member 5 is automatically retracted into the plunger body 40 due to the different pressures. The operating staffs using the safety syringe of the present invention are protected from being stabbed. Furthermore, the sealing rear portion 52 stops air being transported into the sealed space to maintain the lower pressure of the sealed space inside the plunger body 40.

Figure 4A:
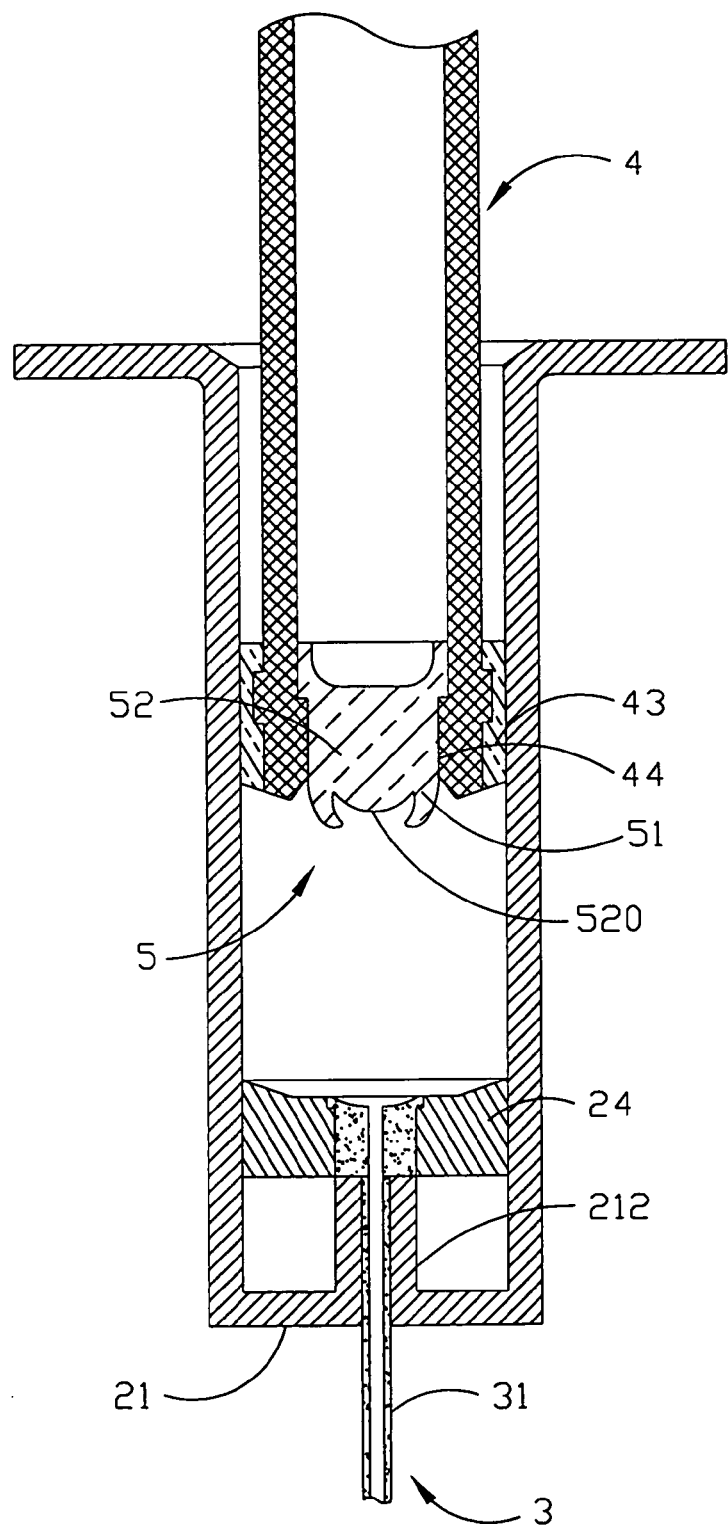
FIGS. 4A-4E illustrate sectional views of a safety syringe of the second embodiment of the present invention
Figure 4B:
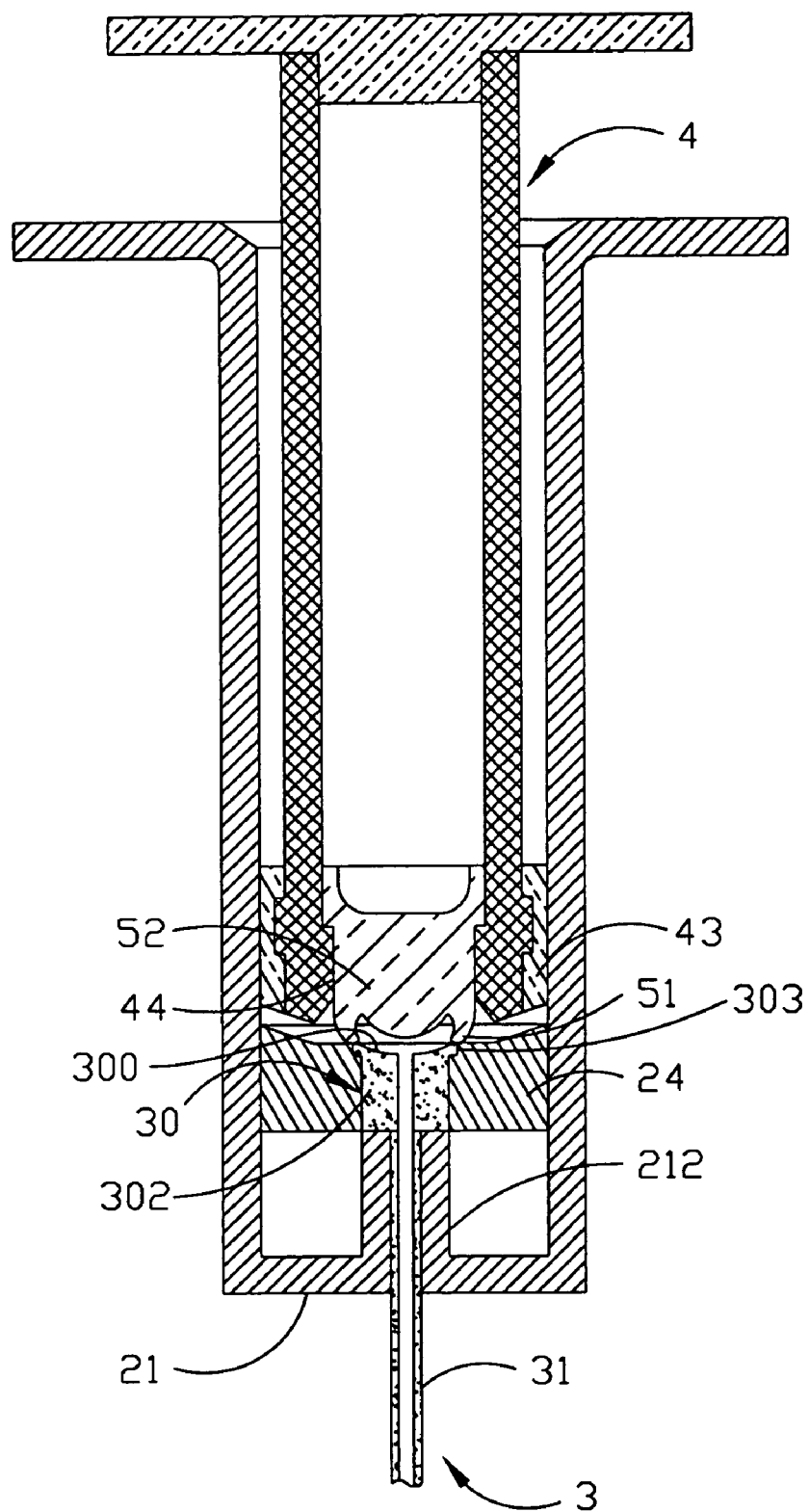
Figure 4C:
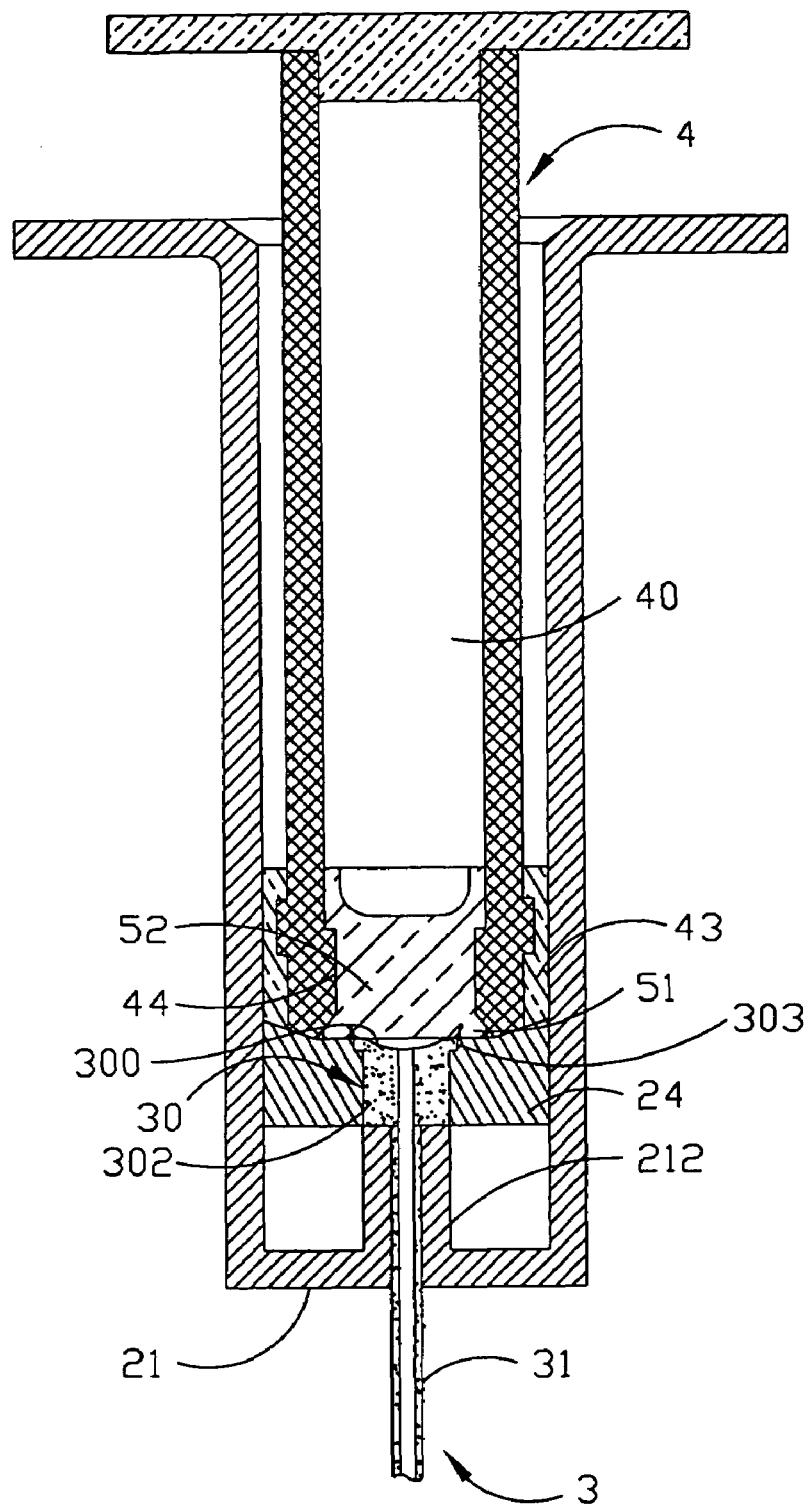
Figure 4D:
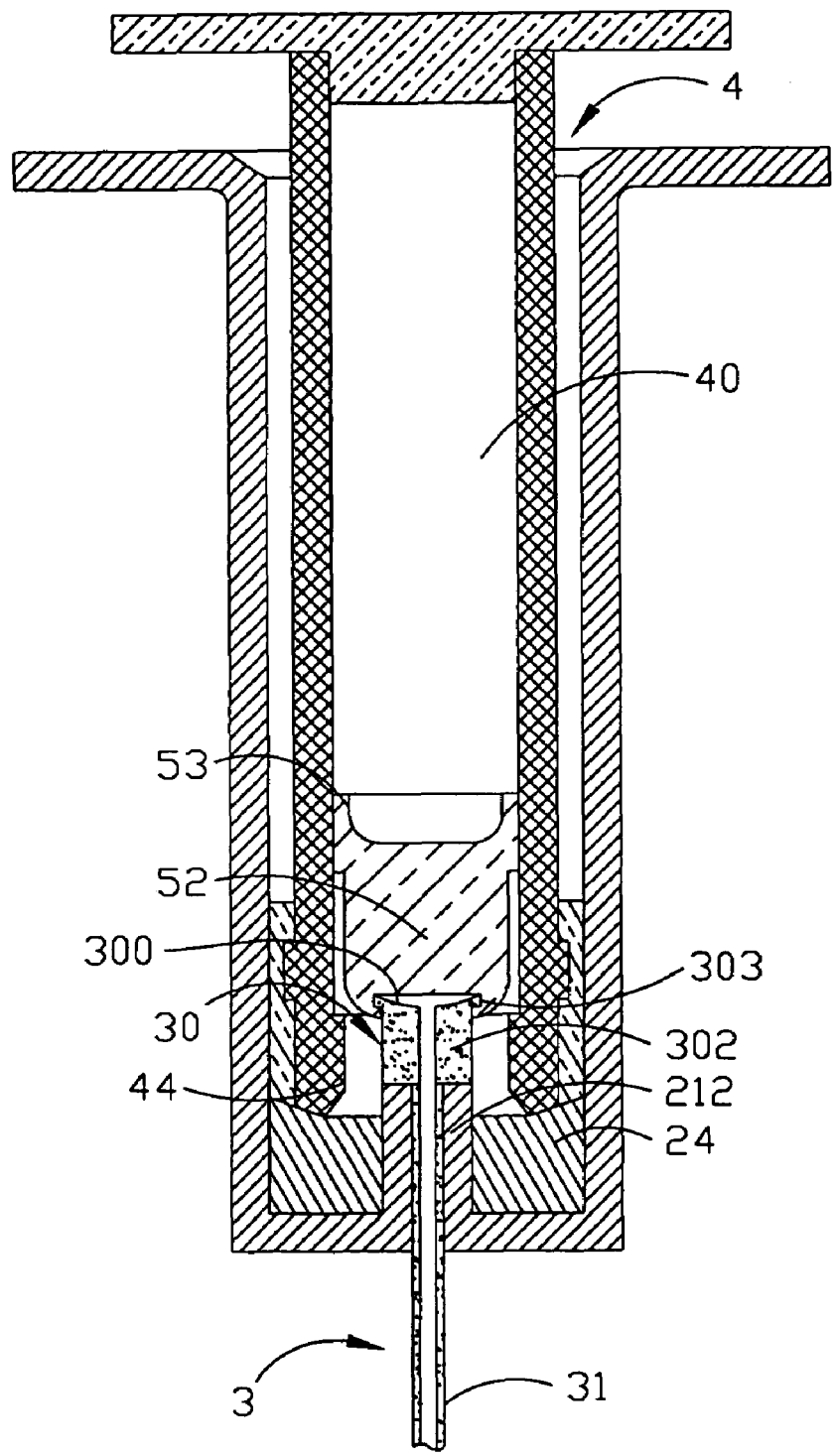
Figure 4E:
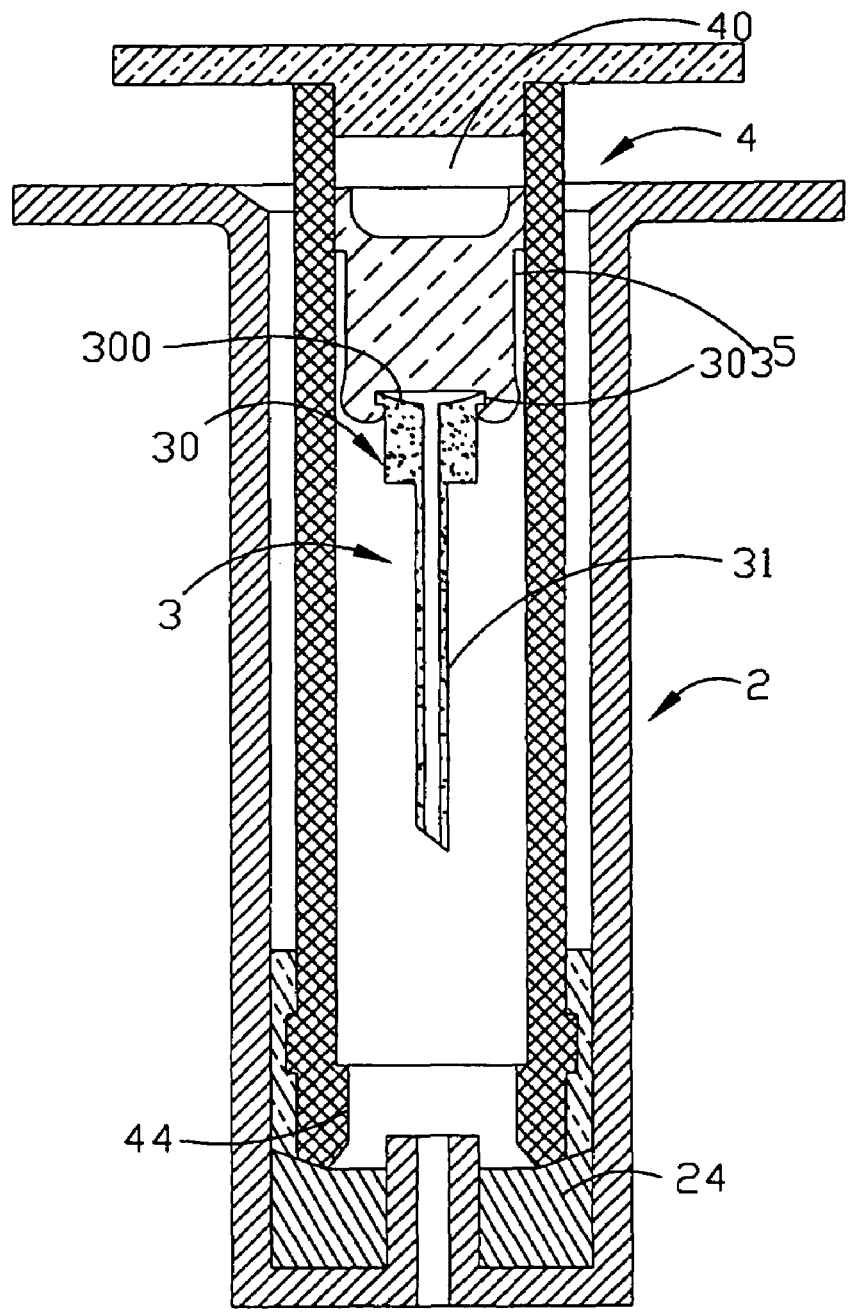

The safety syringe of the second embodiment of the present invention is illustrated as FIGS. 4A-4E. The difference between the first embodiment and the second embodiment of the present invention is the length of the holder-retaining front portion 51 of the flexible-sealing member 5. The holder-retaining front portion 51 can shrink to sleeve the needle unit 3 when the plunger 4 is pushed to contact with the flexible holder-supporting seat 24. As shown in FIG. 4A, the flexible sealing member 5 includes a sealing rear portion 52 and a holder-retaining front portion 51, wherein the external diameter of the sealing rear portion 52 is slightly larger than the internal diameter of the inward flange 44. The inward flange 44 can clench the sealing rear portion 52. Thus, the side in the front end of the inward flange 44 expands slightly and does not contact with the holder-retaining front portion 51. As shown in FIG. 4B, the holder-retaining front portion 51 curves because the holder-retaining front portion 51 contacts with the flexible holder-supporting seat 24 and the needle body 30 when the plunger 4 is pushed forward to contact with the flexible holder-supporting seat 24. As shown in FIG. 4C, the curved holder-retaining front portion 51 curves continuously to be extruded in the space surrounded by the expanded inward flange 44 and the flexible holder-supporting seat 24 when the plunger 4 is continuously pushed. When the inward flange 44 is still pushed forward to push the flexible holder-supporting seat 24, the sealing rear portion 520 of the holder-retaining front portion 51 contacts with the rear opening 300 to stuff the rear opening 300, and the holder-retaining front portion 51 expands due to the outward flange 303. As shown in FIG. 4D, the holder-retaining front portion 51 sleeves the outward flange 303 to combine with the needle unit 3 after the plunger 4 is continuously pushed to push the flexible holder-supporting seat 24, wherein the needle body 30 is fastened by the spacer portion 212. The needle unit 3 is released from the flexible holder-supporting seat 24 when the flexible holder-supporting seat 24 does not contact with the needle unit 3. As shown in FIG. 4E, the flexible sealing member 5 stops moving due to the immovable needle body 30 and then is released from the inward flange 44 because the plunger 4 is continuously pushed to push the flexible holder-supporting seat 24 and release the flexible sealing member 5. Thus the needle unit 3 combined with the flexible sealing member 5 is automatically retracted into the plunger body 40 due to the difference between two different pressures.

Figure 5A:
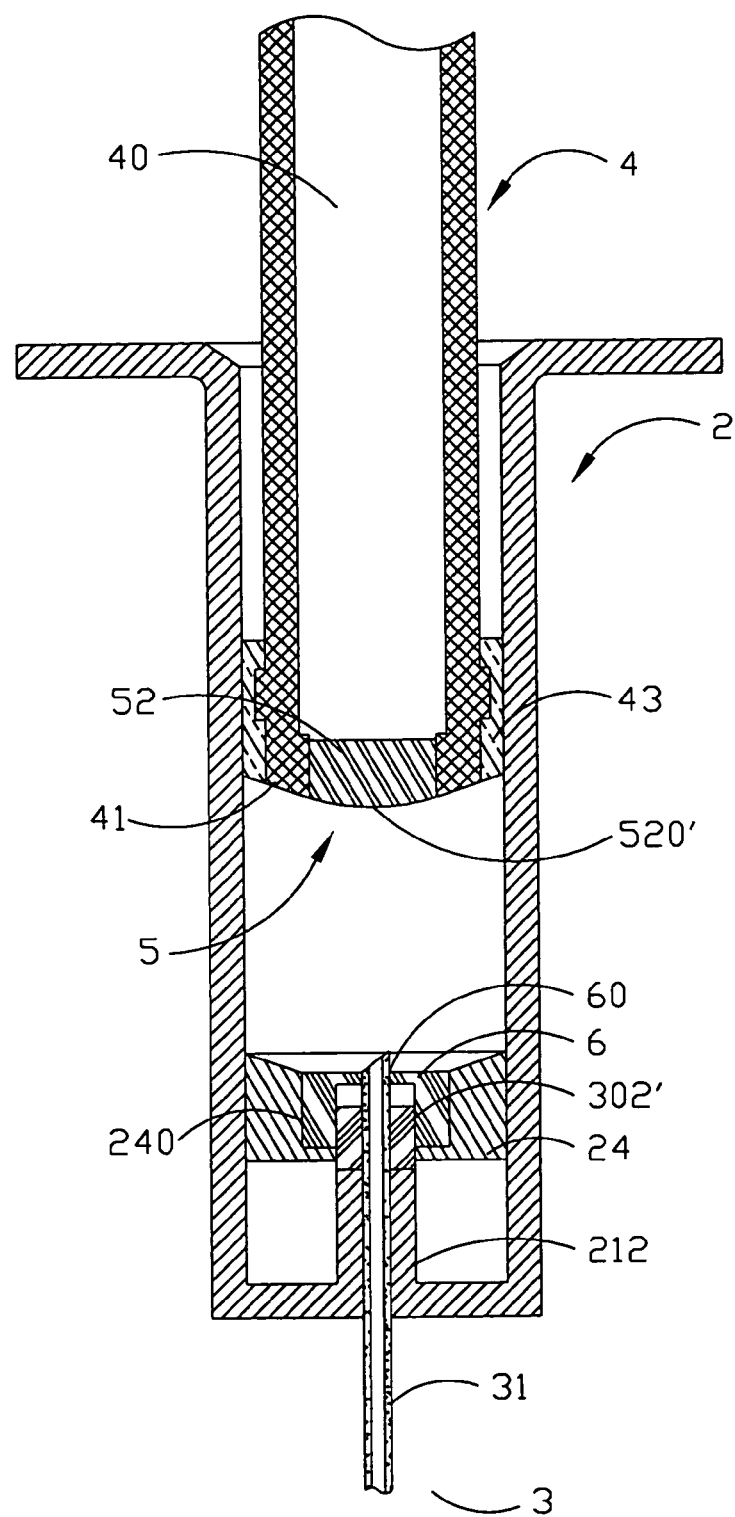
FIGS. 5A-5D illustrate sectional views of a safety syringe of the third embodiment of the present invention.
Figure 5B:
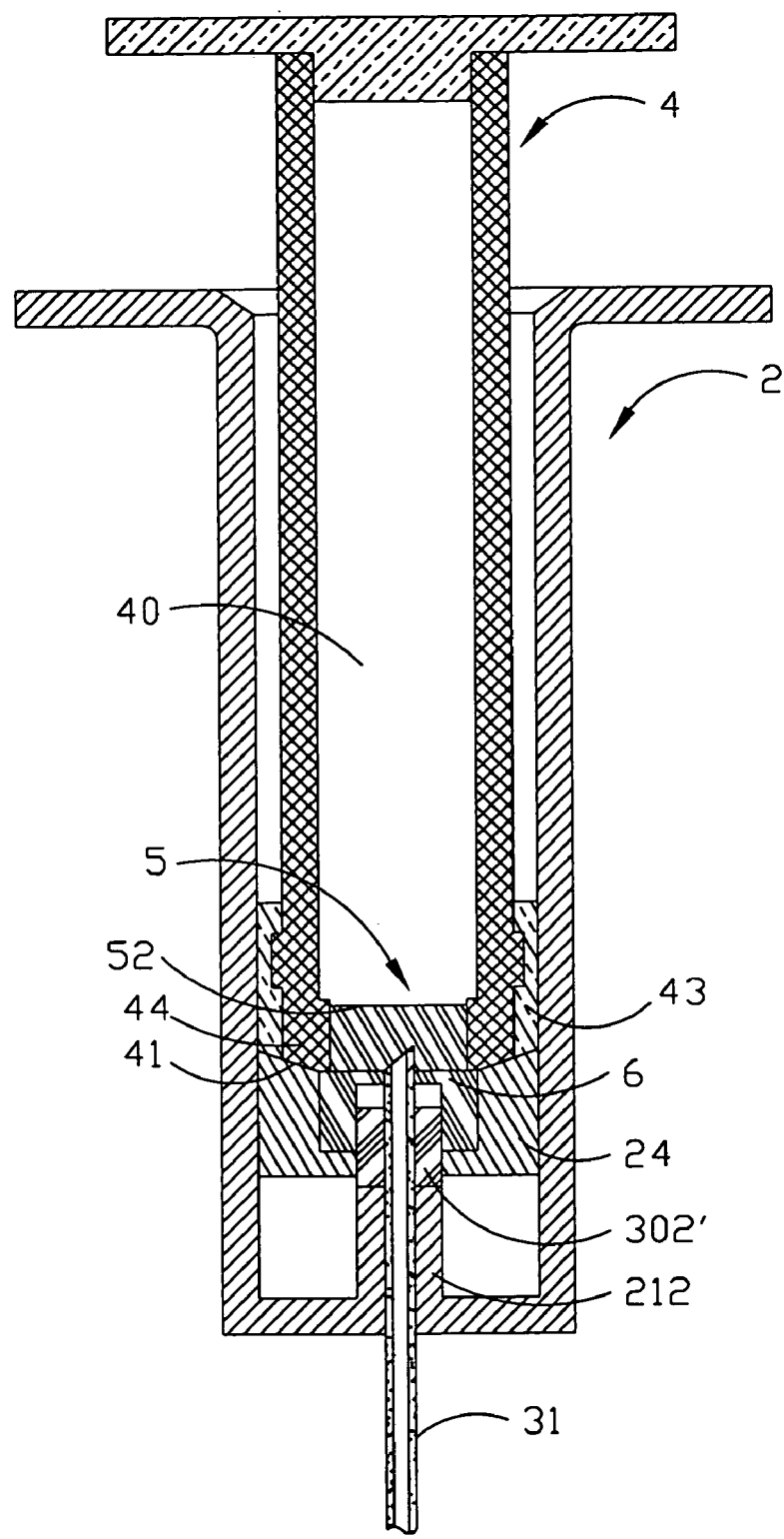
Figure 5C:
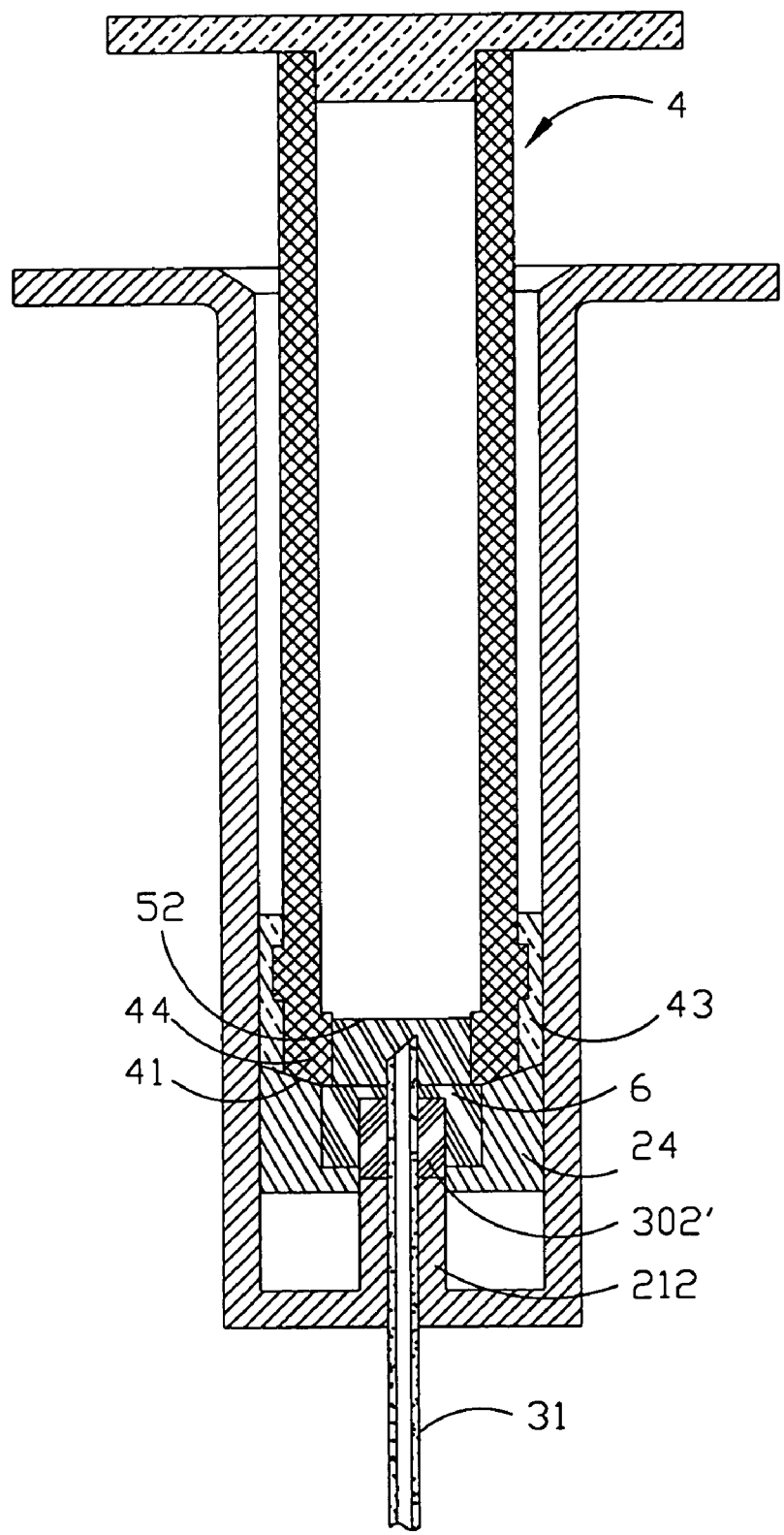
Figure 5D:
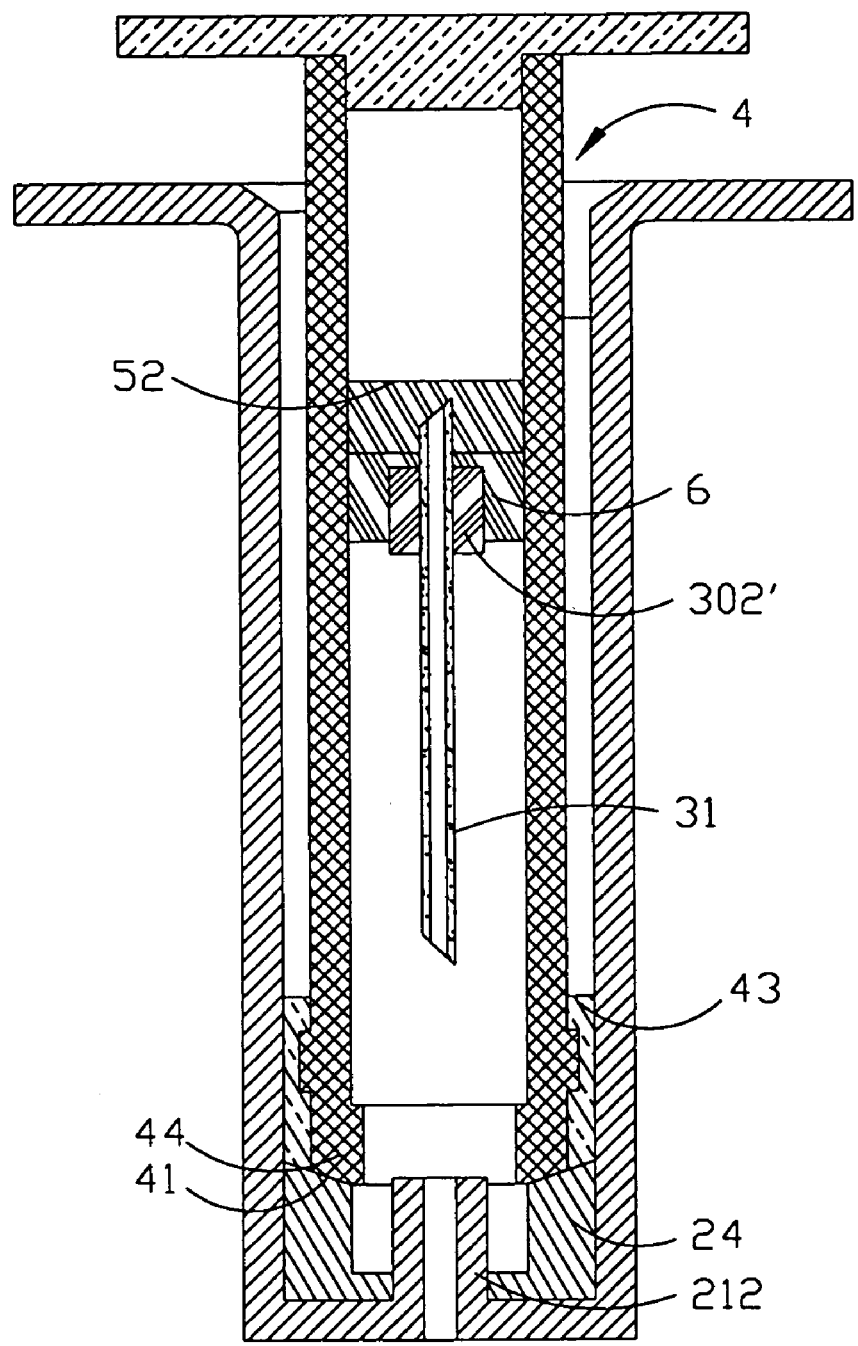

It is to be understood that many modifications and variations of the structures of the annular flexible holder-supporting seat, the sealing member and the needle unit, and the method for disposing the sealing member are possible in light of the above teachings. FIGS. 5A-5D illustrate the third embodiment of the present invention. The side of the central hole 240 of the flexible holder-supporting seat 24 fastens a U-shaped flexible element 6 including a hole 60. The U-shaped flexible element 6 is clenched by the flexible holder-supporting seat 24 and the needle holder 302'. The needle 31 projected from the U-shaped flexible element 6 is clenched by the hole 60. The external diameter of the U-shaped flexible element 6 is slightly larger than the internal diameter of the plunger 4. The needle 31 is fastened by the needle holder 302' and projected from the needle holder 302'. The shape of the flexible sealing member 5 of this embodiment is also different from the shape of the flexible sealing member 5 of the above embodiments of the present invention. The curved projection 520' of the sealing rear portion 52 may be a cambered surface as shown in FIG. 5A. As shown in FIG. 5B, the needle 31 stabs into the curved projection 520' to seal the needle 31 and combine with the U-shaped flexible element 6 and the flexible sealing member 5 when the plunger 4 is pushed to contact with the flexible holder-supporting seat 24. As shown in FIG. 5C, when the plunger 4 is continuously pushed, the flexible holder-supporting seat 24 is pushed by the plunger 4 to slip and release the U-shaped flexible element 6. Because the needle holder 302' is propped up by the spacer portion 212, the U-shaped flexible element 6 is also pushed by the plunger 4 until the bottom of the U-shaped flexible element 6 contacting with the needle holder 302'. The needle 31 stabs into the flexible sealing member 5 deeper when the U-shaped flexible element 6 is pushed forward to contact with the needle holder 302'. The flexible sealing member 5 is pushed by the U-shaped flexible element 6 during the plunger 4, which then pushes the flexible holder-supporting seat 24. After the flexible holder-supporting seat 24 being pushed by the plunger 4 continuously and the inward flange 44 releasing the flexible sealing member 5, the flexible sealing member 5 combining with the needle unit 3 and U-shaped flexible element 6 is withdrawn by the lower pressure inside the plunger 4. As shown in FIG. 5D, the needle unit 3, the U-shaped flexible element 6 and the flexible sealing member 5 is withdrawn into the plunger body 40 due to the pressure.

Figure 6:
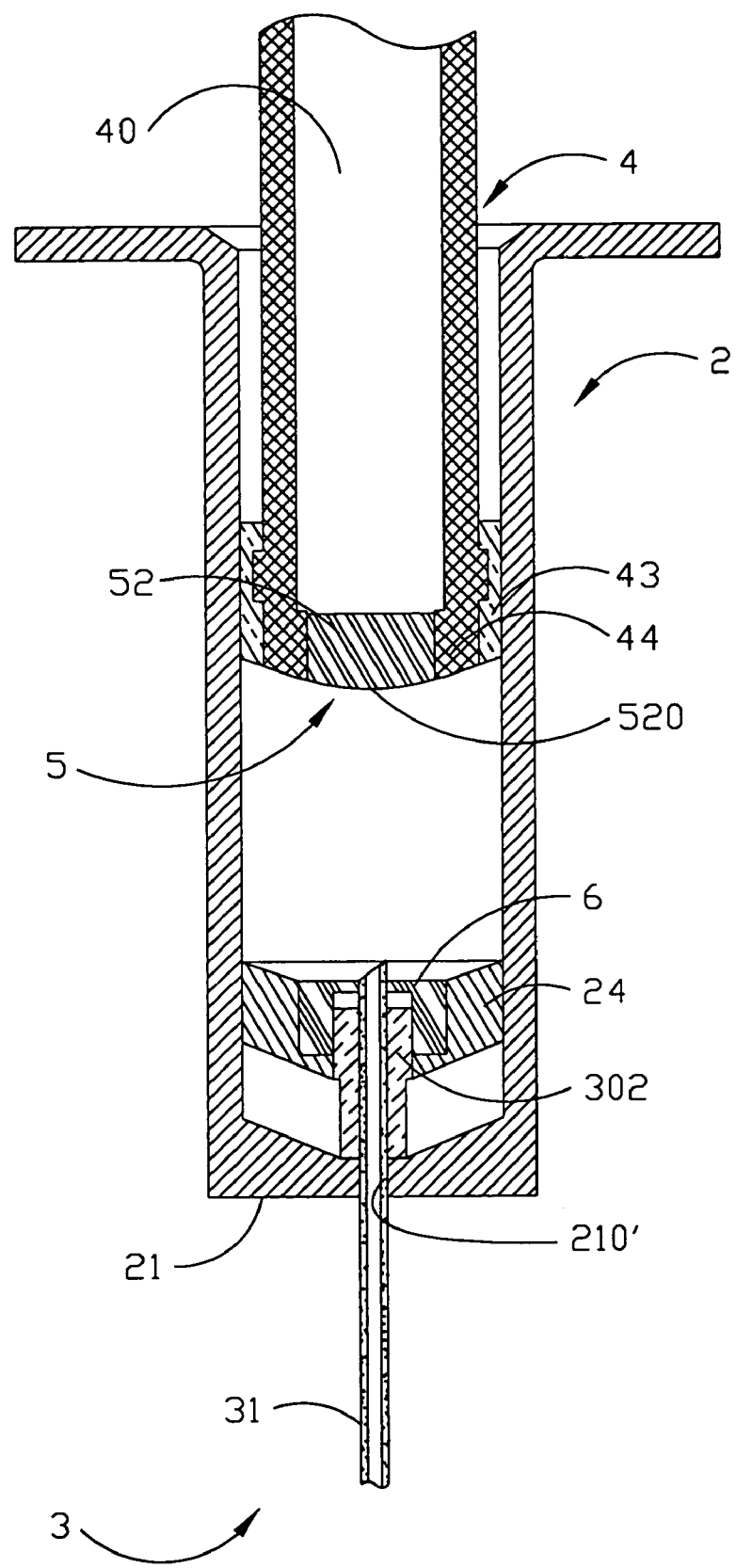
FIG. 6 illustrates a sectional view of a safety syringe of the fourth embodiment of the present invention.

As shown in FIG. 6, the fourth embodiment of the present invention provides a safety syringe including a syringe barrel 2 with a different front-end wall 21. The front-end wall 21 includes a front opening 210' for fastening a needle 31, wherein the needle 31 projects from the front end wall 21. The needle 31 stabs into the sealing rear portion 520 to seal the needle 31 and combine the needle unit 3 with the U-shaped flexible element 6 and the flexible sealing member 5 when the plunger 4 is pushed to contact with the flexible holder-supporting seat 24. When the plunger 4 is continuously pushed, the flexible holder-supporting seat 24 is pushed by the plunger 4 to slip and release the U-shaped flexible element 6. Because the 210 prop up the needle holder 302, the U-shaped flexible element 6 is also pushed by the plunger 4 until the bottom of the U-shaped flexible element 6 contacting with the needle holder 302. The needle 31 stabs into the flexible-sealing member 5 deeper when the U-shaped flexible element 6 is pushed to contact with the needle holder 302. The flexible sealing member 5 is pushed by the U-shaped flexible element 6 during the plunger 4 pushes the flexible holder-supporting seat 24. After the flexible holder-supporting seat 24 being continuously pushed by the plunger 4 and the inward flange 44 releasing the flexible sealing member 5, the flexible sealing member 5 combining with the needle unit 3 and U-shaped flexible element 6 is withdrawn by the lower pressure inside the plunger 4. The needle unit 3, the U-shaped flexible element 6 and the flexible-sealing member 5 is withdrawn into the plunger body 40 due to the pressure.

Figure 7A:
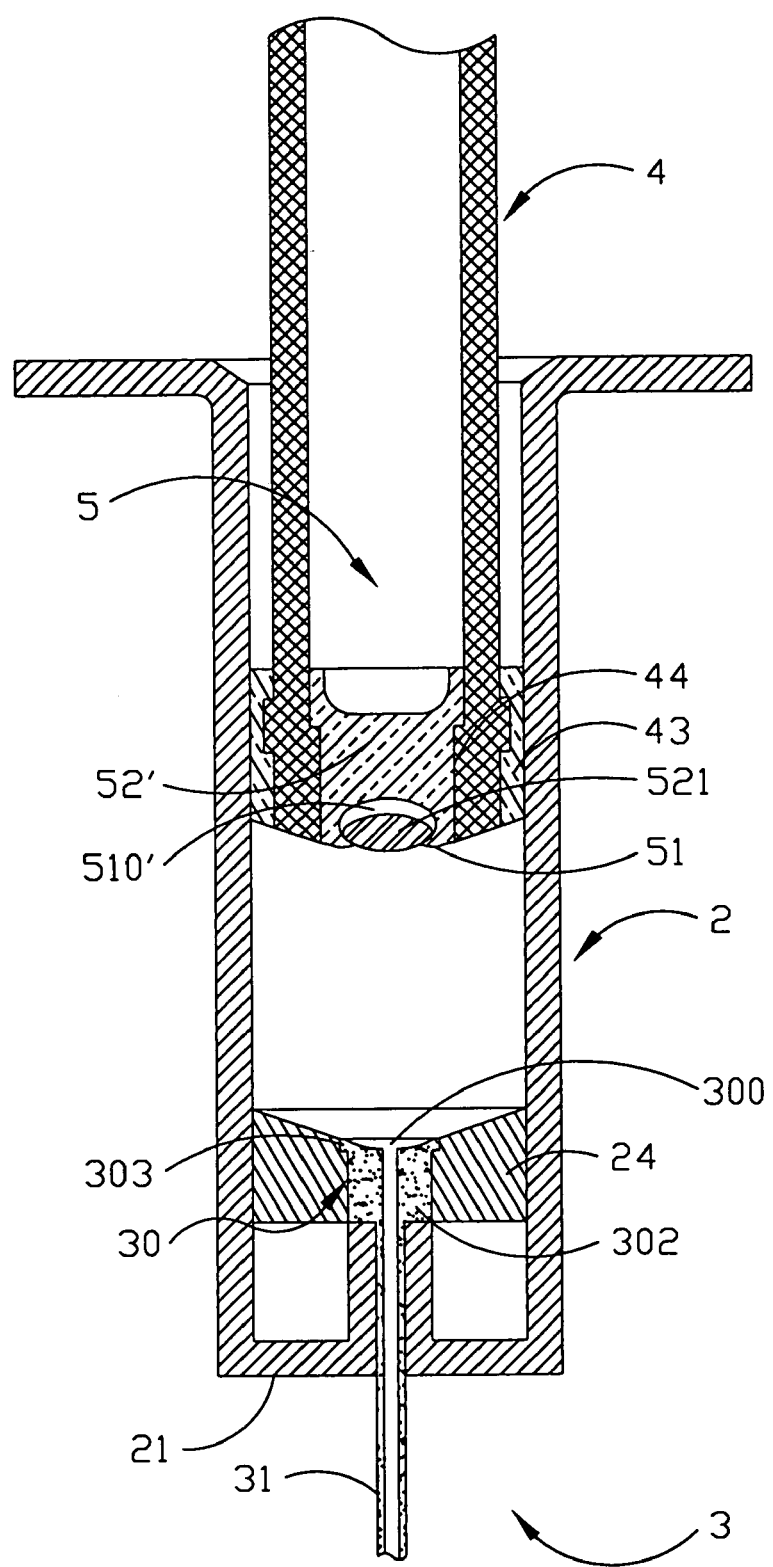
FIGS. 7A-7D illustrate sectional views of a safety syringe of the fifth embodiment of the present invention
Figure 7B:
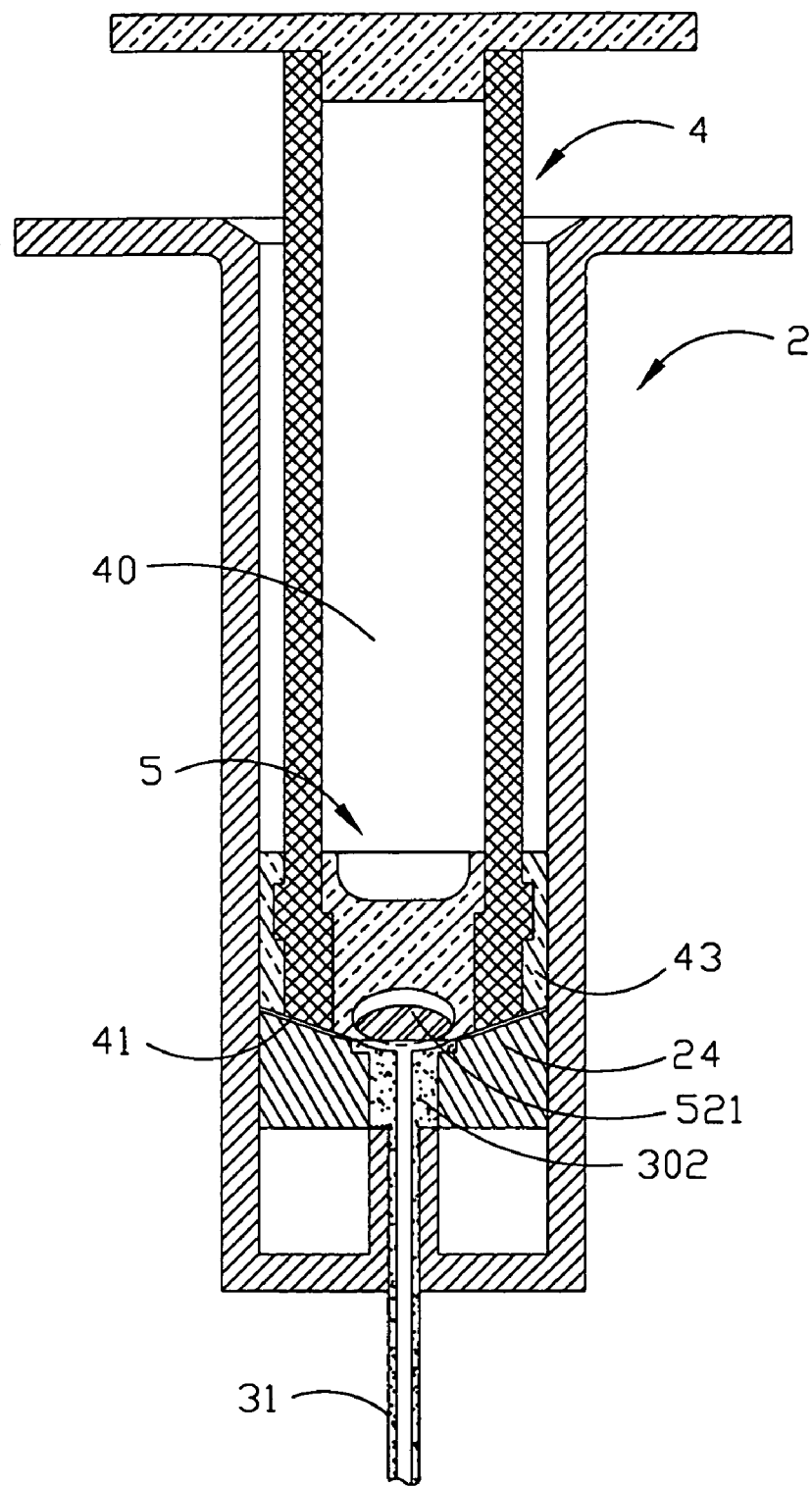
Figure 7C:
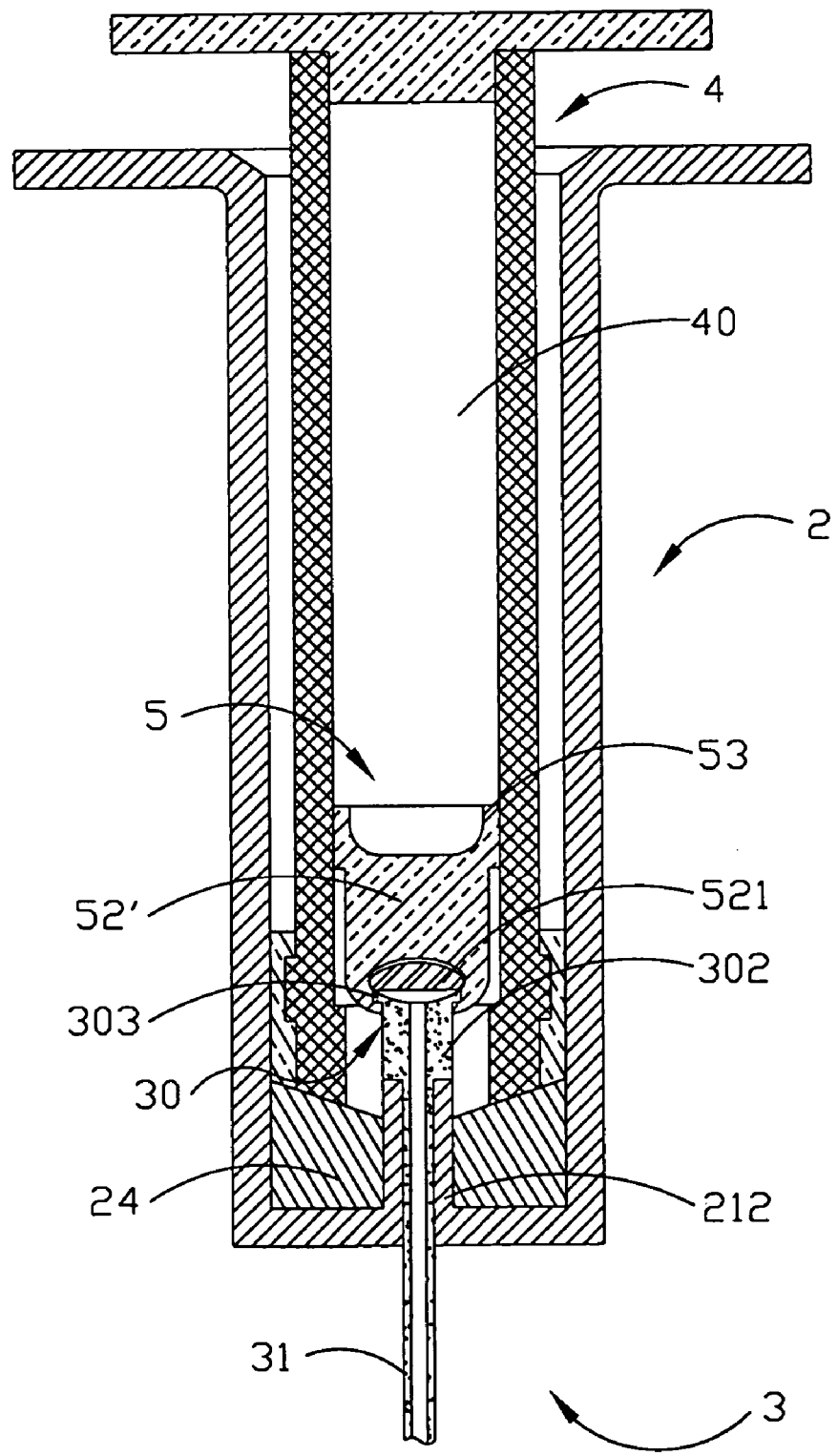
Figure 7D:
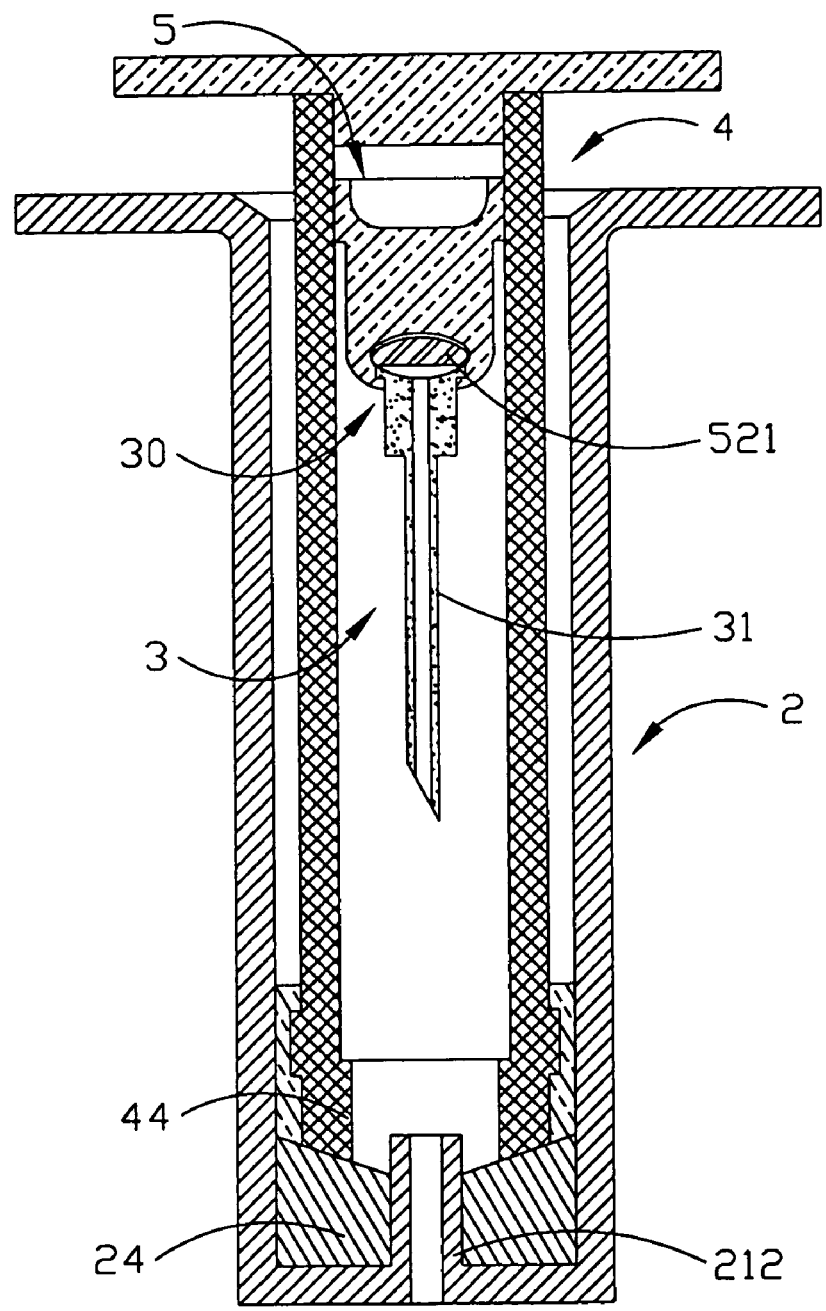

The fifth embodiment of the present invention is illustrated as FIGS. 7A-7D. The difference between the first embodiment and the fifth embodiment of the present invention is the structure of the flexible sealing member 5. As shown in FIG. 7A, the flexible sealing member 5 includes a holder-retaining front portion 51, a blind hole 510' and a piston body 521, wherein the blind hole 510' is formed within the holder-retaining front portion 51. As shown in FIG. 7B, the holder-retaining front portion 51 becomes slightly flat, because the holder-retaining front portion 51 contacts with the needle body 30 when the plunger 4 is pushed forward to be close to the flexible holder-supporting seat 24. As shown in FIG. 7C, the slightly flat holder-retaining front portion 51 is continuously pushed to combine with the outward flange 303 when the plunger 4 is continuously pushed. When the inward flange 44 is still pushed forward to push the flexible holder-supporting seat 24, the piston body 521 contacts with the rear opening 300 to stuff the rear opening 300 to lock the needle 31 from injecting the medicament. The holder-retaining front portion 51 sleeves the outward flange 303 to combine with the needle unit 3 after the plunger 4 is pushed continuously to push the flexible holder-supporting seat 24, wherein the needle body 30 is propped by the spacer portion 212. As shown in FIG. 7D, the needle unit 3 is released from the flexible holder-supporting seat 24 when the flexible holder-supporting seat 24 does not contact with the needle unit 3. The flexible sealing member 5 stops moving due to the immovable needle body 30 and then is released from the inward flange 44 because the plunger 4 is continuously pushed to push the flexible holder-supporting seat 24 and release the flexible sealing member 5. Thus the needle unit 3 combined with the flexible sealing member 5 and the piston body 521 is automatically retracted into the plunger body 40 due to the different pressures.

Figure 8:
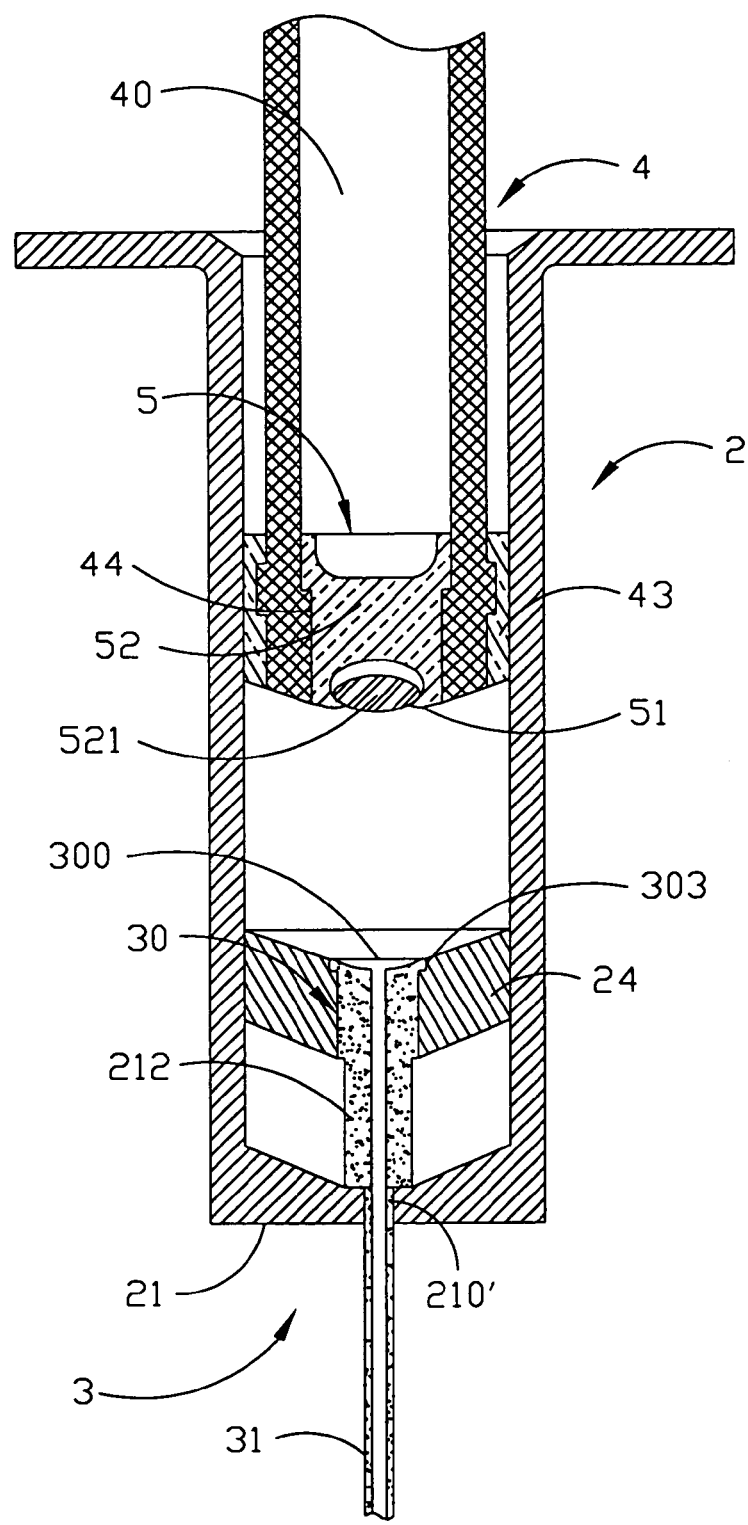
FIG. 8 illustrates a sectional view of a safety syringe of the sixth embodiment of the present invention.

As shown in FIG. 8, the sixth embodiment of the present invention provides a safety syringe including a syringe barrel 2 with a different front-end wall 21. The front-end wall 21 includes a front opening 210' for fastening a needle 31, wherein the needle 31 projects from the front end wall 21. The holder-retaining front portion 51 is pushed to combine with the outward flange 303 when the plunger 4 is pushed to be close to the flexible holder-supporting seat 24. When the inward flange 44 is still pushed forward to push the flexible holder-supporting seat 24, the piston body 521 contacts with the rear opening 300 to stuff the rear opening 300 to lock the needle 31 from injecting the medicament. The holder-retaining front portion 51 sleeves the outward flange 303 to combine with the needle unit 3 after the plunger 4 is continuously pushed to push the flexible holder-supporting seat 24, wherein the needle body 30 is propped by the spacer portion 212. The needle unit 3 is released from the flexible holder-supporting seat 24 when the flexible holder-supporting seat 24 does not contact with the needle unit 3. The flexible sealing member 5 stops moving due to the immovable needle body 30 and the piston body 521, and then the flexible sealing member 5 is released from the inward flange 44 because the plunger 4 is continuously pushed to push the flexible holder-supporting seat 24. Thus the needle unit 3 combined with the flexible sealing member 5 and the piston body 521 is automatically retracted into the plunger body 40 due to the difference between two different pressures.

Figure 9A:
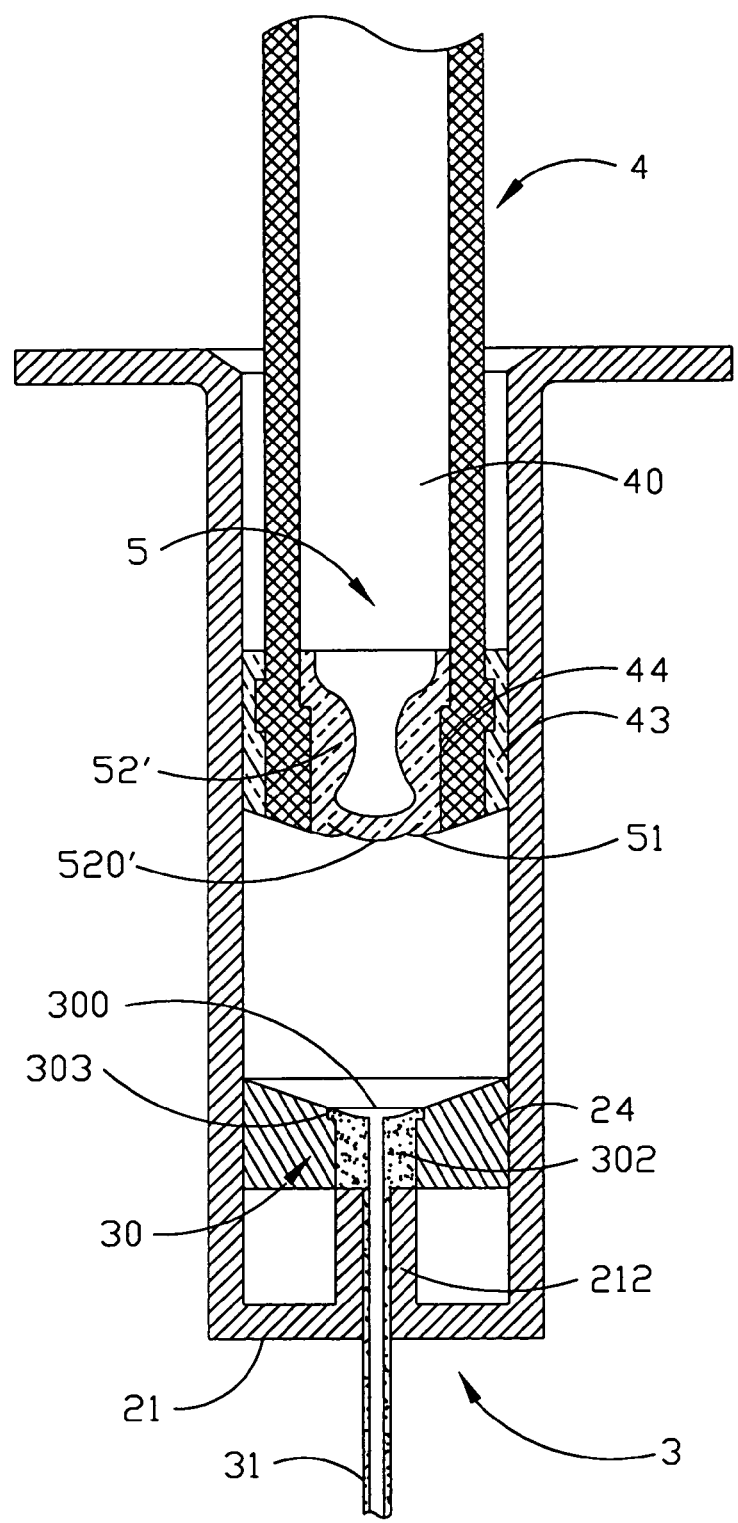
FIGS. 9A-9B illustrate sectional views of a safety syringe of the seventh embodiment of the present invention.
Figure 9B:
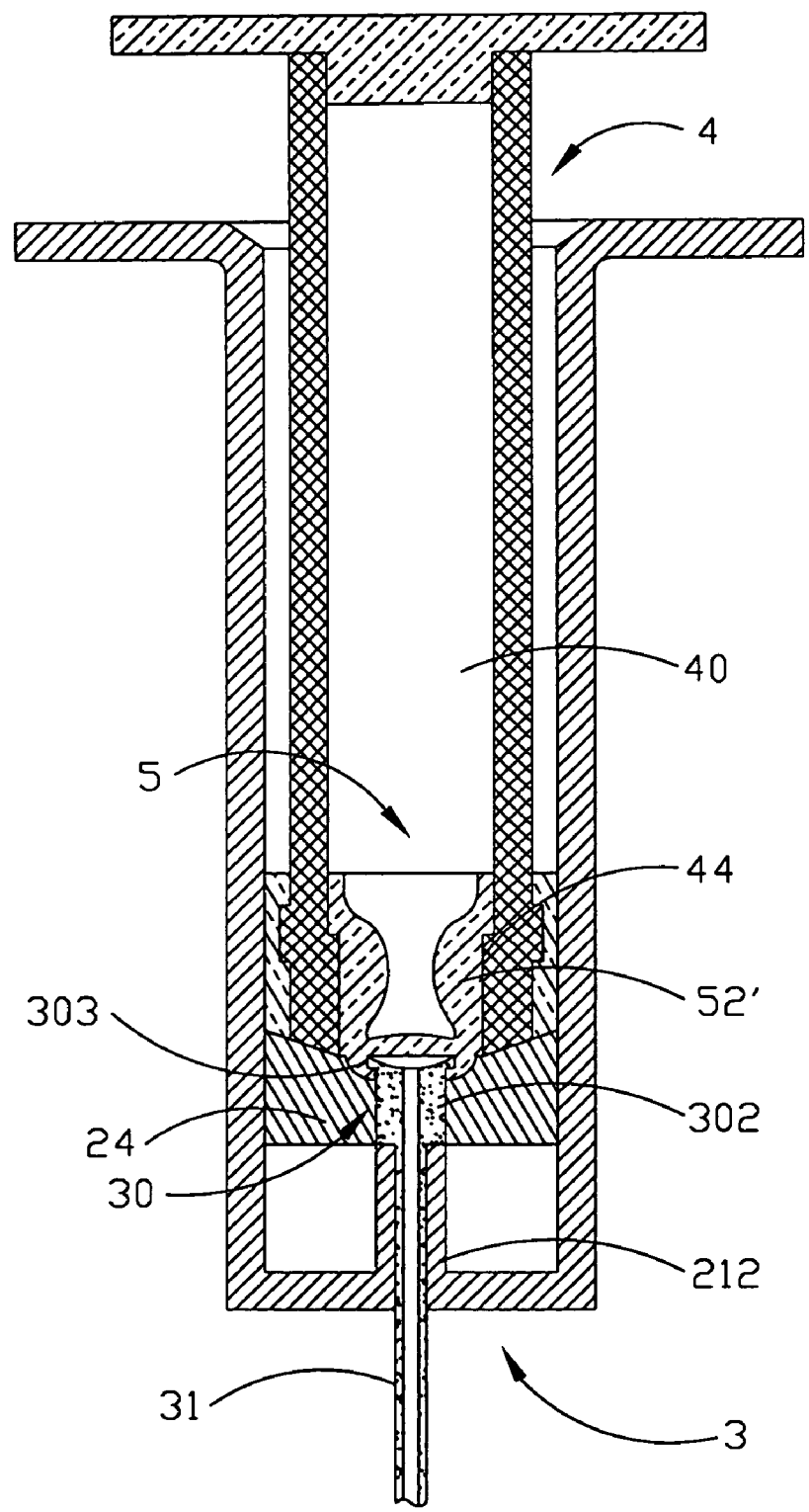

The seventh embodiment of the present invention is illustrated as FIG. 9A and FIG. 9B. The difference between the fifth embodiment and the seventh embodiment of the present invention is the structure of the flexible sealing member 5. As shown in FIG. 9A, the flexible sealing member 5 includes a holder-retaining front portion 51, a sealing rear portion 52' and a curved projection 520', wherein the holder-retaining front portion 51 is a hollow awl extended forward from the hollow sealing rear portion 52'. The sealing rear portion 52' includes a hollow space therein. The external diameter of the holder-retaining front portion 51 is as small as that extending forward. The surface of the curved projection 520' is a cambered surface formed on the hollow sealing rear portion 52'. As shown in FIG. 9B, the holder-retaining front portion 51 is pushed to combine with the outward flange 303 when the plunger 4 is pushed forward to be close to the flexible holder-supporting seat 24 when the plunger 4 is pushed continuously. When the inward flange 44 is still pushed forward to push the flexible holder-supporting seat 24, the curved projection 520' contacts with the rear opening 300 to stuff the rear opening 300 to prevent the needle 31 from injecting the medicament. The holder-retaining front portion 51 sleeves the outward flange 303 to combine with the needle unit 3 after the plunger 4 is pushed continuously to push the flexible holder-supporting seat 24, wherein the needle body 30 is propped by the spacer portion 212. The needle body 30 is released from the flexible holder-supporting seat 24 when the flexible holder-supporting seat 24 does not contact with the needle unit 3. The flexible sealing member 5 stops moving due to the immovable needle body 30 and is then released from the inward flange 44 because the plunger 4 is continuously pushed to push the flexible holder-supporting seat 24 and release the flexible sealing member 5. Thus the needle unit 3 combined with the flexible sealing member 5 is automatically retracted into the plunger body 40 due to the difference between two different pressures.

Figure 10:
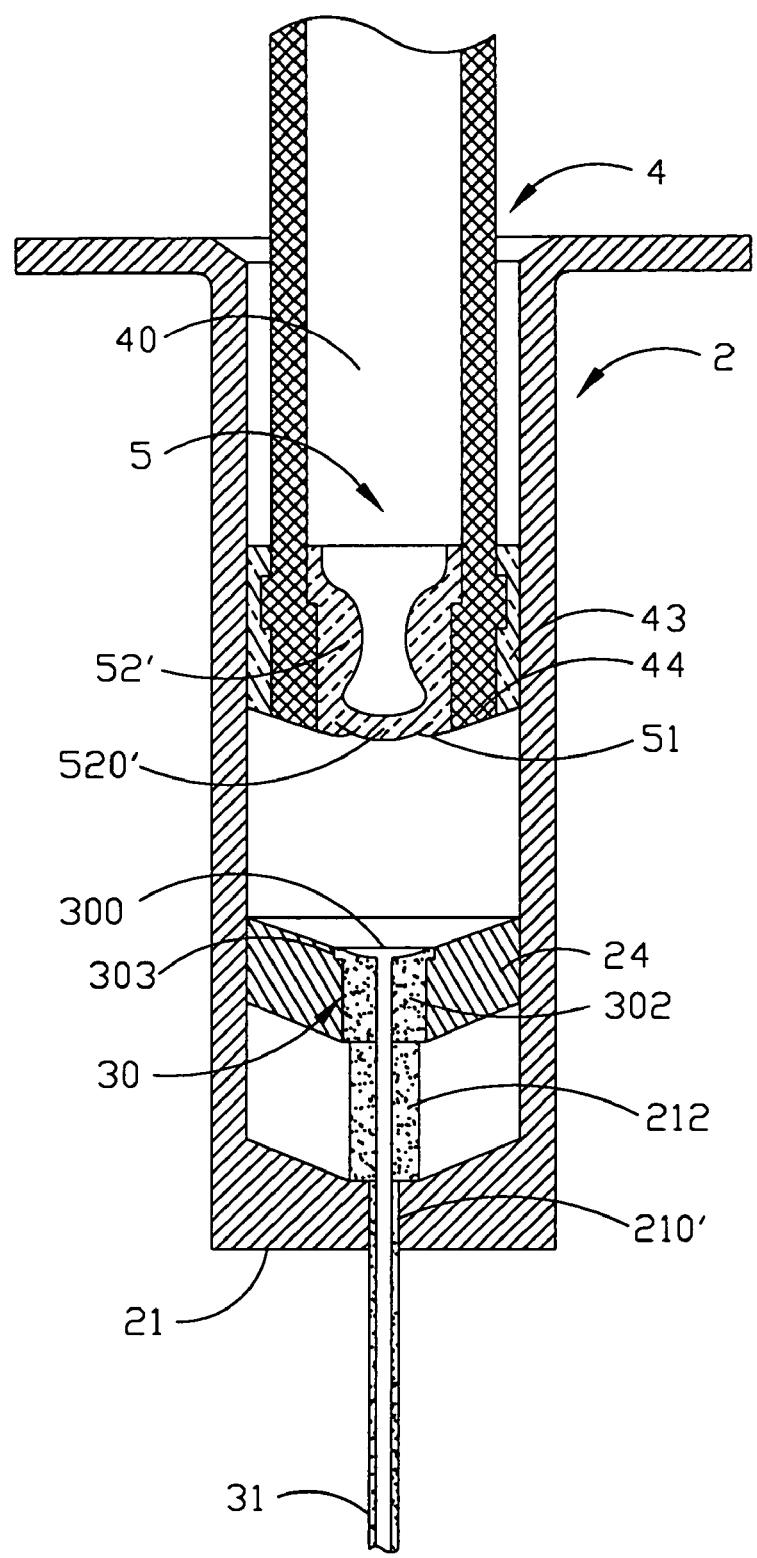
FIG. 10 illustrates a sectional view of a safety syringe of the eighth embodiment of the present invention.

As shown in FIG. 10, the eighth embodiment of the present invention provides a safety syringe including a syringe barrel 2 with a different front-end wall 21. The front-end wall 21 includes a front opening 210' for fastening a needle 31, wherein the needle 31 projects from the front end wall 21. The holder-retaining front portion 51 is pushed to sleeve and combine with the outward flange 303 when the plunger 4 is pushed to be close to the flexible holder-supporting seat 24. When the inward flange 44 is still pushed forward to push the flexible holder-supporting seat 24, the curved projection 520' contacts with the rear opening 300 to stuff the rear opening 300 to prevent the needle 31 from injecting the medicament. The holder-retaining front portion 51 sleeves the outward flange 303 to combine with the needle unit 3 after the plunger 4 is continuously pushed to push the flexible holder-supporting seat 24, wherein the needle holder 302 is propped by the spacer portion 212. The needle unit 3 is released from the flexible holder-supporting seat 24 when the flexible holder-supporting seat 24 does not contact with the needle unit 3. The flexible sealing member 5 stops moving due to the immovable needle body 30, and then the flexible sealing member 5 is released from the inward flange 44 because the plunger 4 is continuously pushed to push the flexible holder-supporting seat 24. Thus the needle unit 3 combined with the flexible sealing member 5 is automatically retracted into the plunger body 40 due to the difference between two different pressures.

Figure 11A:
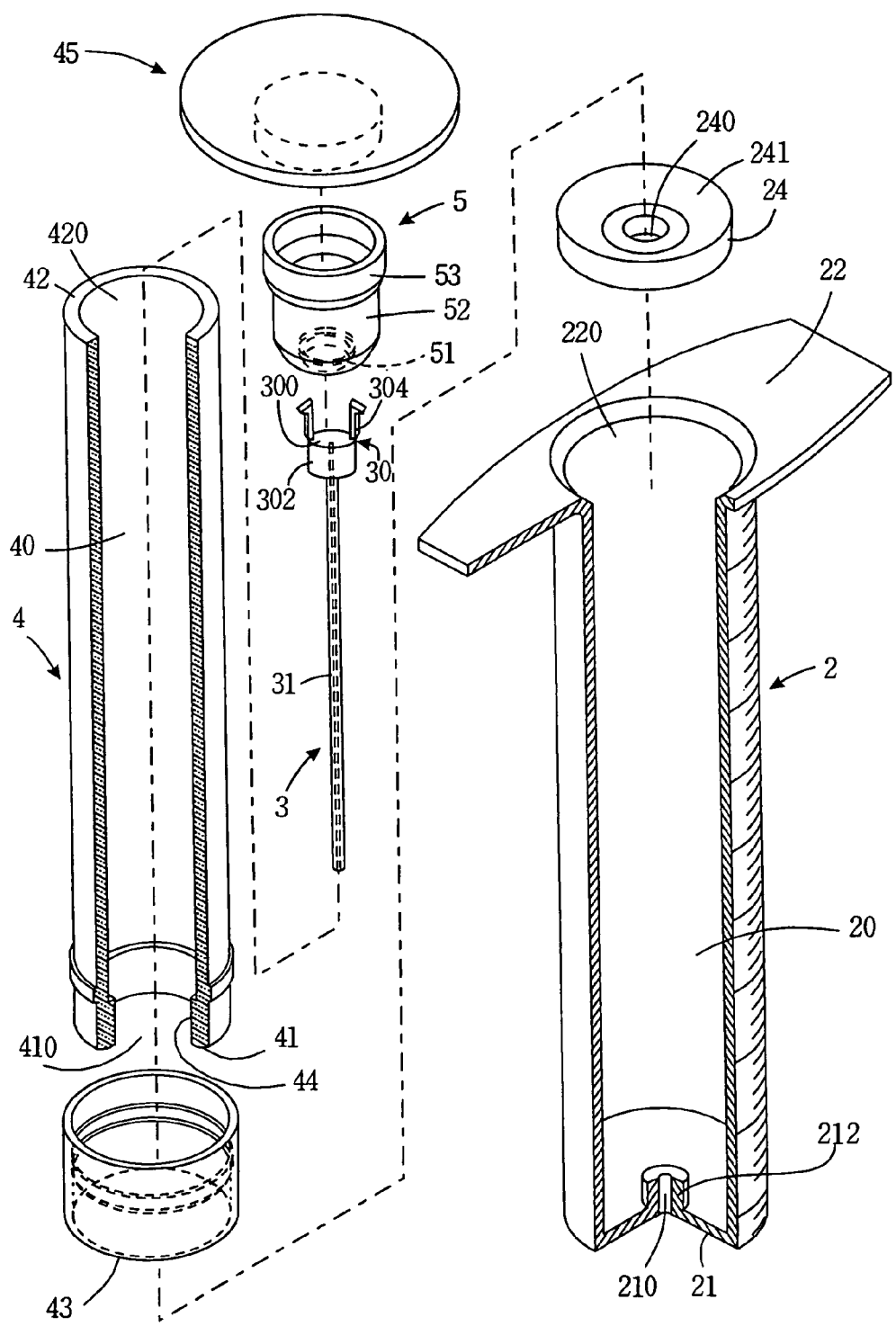
FIGS. 11A-11C illustrate sectional views of a safety syringe of the ninth embodiment of the present invention.
Figure 11B:
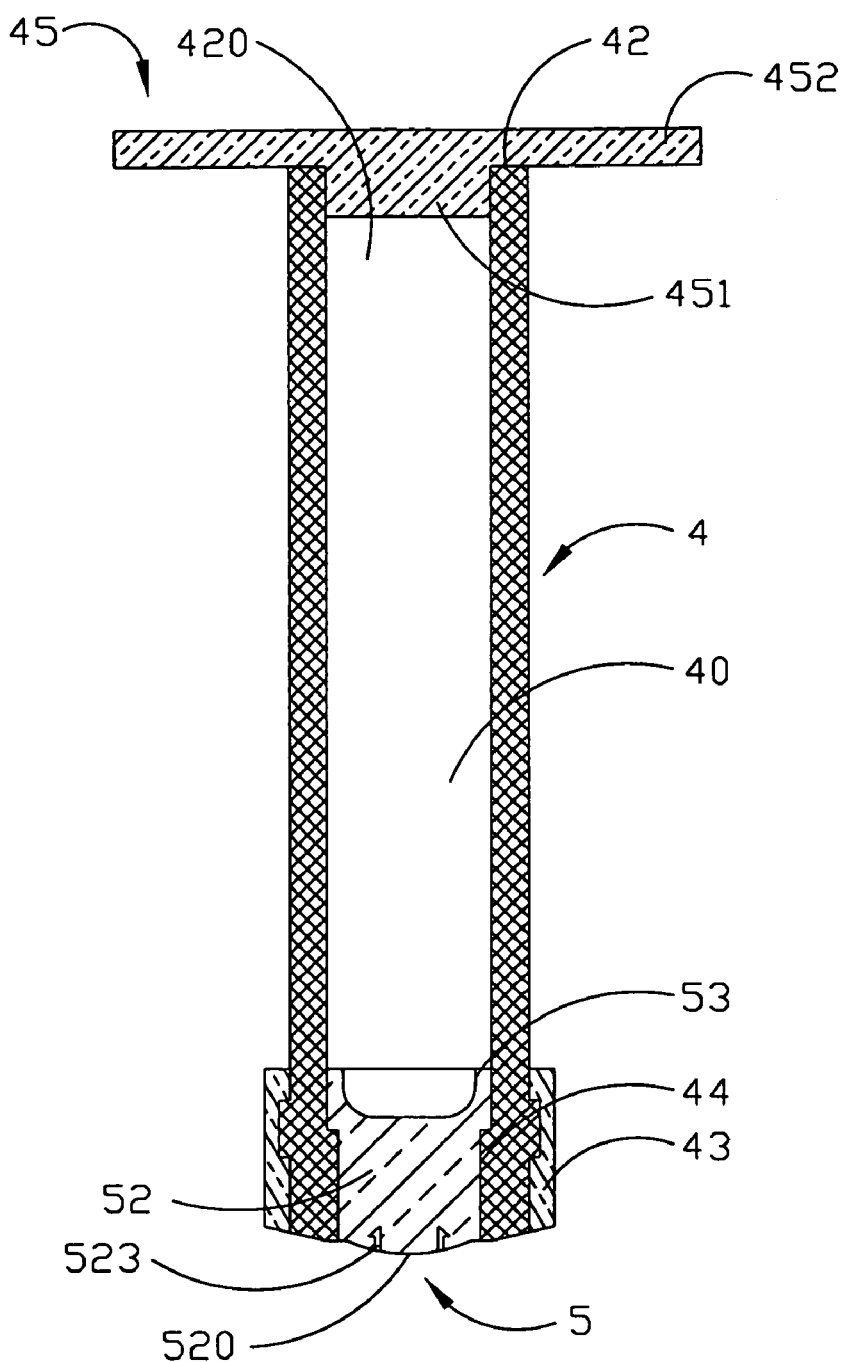
Figure 11C:
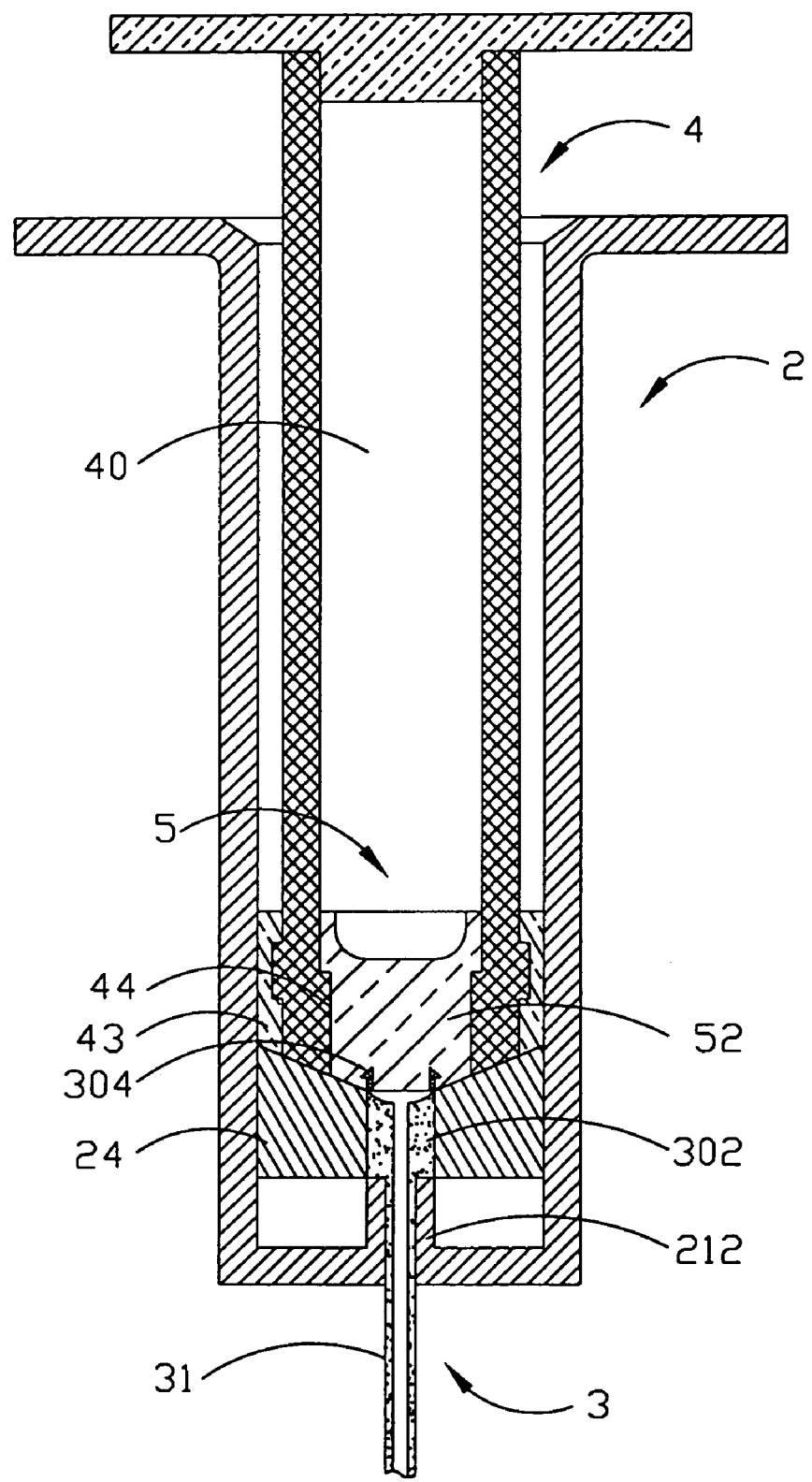

The ninth embodiment of the present invention is illustrated as FIG. 11A to FIG. 11C. The difference between the ninth embodiment and the first embodiment of the present invention is the structure of the needle unit 3 and the flexible-sealing member 5. As shown in FIG. 11A, that the needle unit 3 includes a needle holder 302 and a crook 304, wherein the crook 304 is fastened on the needle holder 302. As shown in FIG. 1B, the flexible sealing member 5 includes a sealing rear portion 52 and a curved projection 520, wherein the curved projection 520 is a cambered surface. An opening 523 is formed inside the sealing rear portion 52 for wedging the crook 304 of the needle body 30. As shown in FIG. 11C, the opening 523 of the sealing rear portion 52 is pushed to wedge the crook 304 for combining with the needle body 30 when the plunger 4 is pushed forward to be close to the flexible holder-supporting seat 24. When the open front end 41 of the plunger 4 is pushed to be close to the flexible holder-supporting seat 24, the curved projection 520 contacts with the rear opening 300 to stuff the rear opening 300 to lock the needle 31 from injecting the medicament. The flexible sealing member 5 stops moving due to the immovable needle body 30 propped by the spacer portion 212, after the plunger 4 is continuously pushed to push the flexible holder-supporting seat 24. The needle body 30 is released from the flexible holder-supporting seat 24 when the flexible holder-supporting seat 24 does not contact with the needle unit 3. The flexible sealing member 5 stops moving due to the immovable needle body 30 and then is released from the inward flange 44 because the plunger 4 is continuously pushed to push the flexible holder-supporting seat 24 and release the flexible sealing member 5. Thus the needle unit 3 combined with the flexible sealing member 5 is automatically retracted into the plunger body 40 due to the difference between two different pressures.

Figure 12:
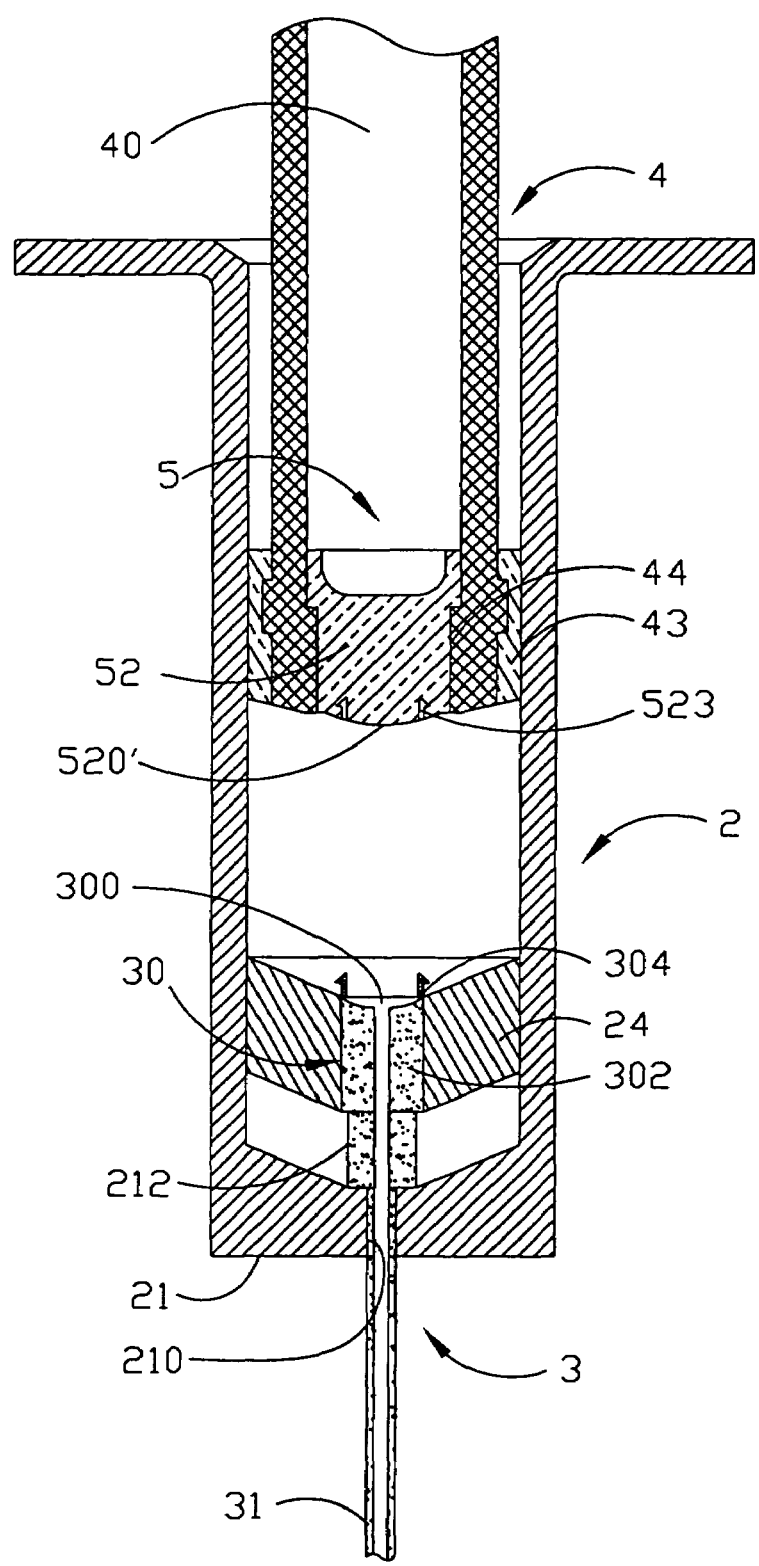
FIG. 12 illustrates a sectional view of a safety syringe of the tenth embodiment of the present invention.

As shown in FIG. 12, the tenth embodiment of the present invention provides a safety syringe including a syringe barrel 2 with a different front-end wall 21. The front-end wall 21 includes a front opening 210 for fastening a needle 31, wherein the needle 31 projects from the front-end wall 21. The curved projection 520 is pushed to wedge the crook 304 and combine with the needle body 30 when the plunger 4 is pushed to be close to the flexible holder-supporting seat 24. When the inward flange 44 is still pushed forward to push the flexible holder-supporting seat 24, the curved projection 520 contacts with the rear opening 300 to stuff the rear opening 300 to prevent the needle 31 from injecting the medicament. The flexible sealing member 5 stops moving due to the immovable needle body 30 propped by the spacer portion 212, after the plunger 4 is continuously pushed to push the flexible holder-supporting seat 24. The needle body 30 is released from the flexible holder-supporting seat 24 when the flexible holder-supporting seat 24 does not make contact with the needle body 30. The flexible sealing member 5 stops moving due to the immovable needle body 30, and then the flexible sealing member 5 is released from the inward flange 44 because the plunger 4 is continuously pushed to push the flexible holder-supporting seat 24. Thus the needle unit 3 combined with the flexible sealing member 5 is automatically retracted into the plunger body 40 due to the difference between two different pressures.

The present invention provides a safety syringe including simple elements. The present invention also economizes the cost for manufacturing the safety syringes and effectively protects the operating staff from becoming stabbed.

Obviously, many modifications and variations of the present invention are possible in light of the above teachings. It is to be understood that within the scope of the appended claims, the present invention may be practiced other than as specifically described herein.

Although the specific embodiments have been illustrated and described, it will be obvious to those skilled in the art that various modifications may be made without departing from what is intended to be limited solely by the appended claims.

What is claimed is:

1. A safety syringe, comprising:
   a syringe barrel including a barrel body with a front opening, a rear opening, a front end wall and a rear end wall, wherein a cross-sectional area of said front opening is smaller than a cross-sectional area of said rear opening, a spacer portion is disposed integrally within said barrel body and is penetrated by said front opening;
   a flexible holder-supporting seat being disposed movably within said syringe barrel and on said spacer portion, wherein said flexible holder-supporting seat includes a central hole formed therethrough;
   a needle unit including a needle holder and a needle penetrating said needle holder, said needle unit is disposed movably within said front end wall, said needle holder being sleeved by said central hole of said flexible holder-supporting seat on said spacer portion, wherein a rear opening is formed in said rear end of said needle holder, said needle penetrates said needle holder and said spacer portion and is projected from said front opening;
   a plunger including a front end with a front opening and an inward flange, a rear end and a plunger body formed between said front end and said rear end, a cross-sectional area of said front opening being larger than an external diameter of said needle holder, said plunger being disposed movably within said syringe barrel; and
   a flexible sealing member sleeved by said inward flange to seal said front opening of said plunger, said flexible sealing member combining with said needle unit after said plunger being pushed to be close to said flexible holder-supporting seat, said flexible holder-supporting seat being sleeved on said spacer portion, and then said needle unit being released from said flexible holder-supporting seat due to said plunger, wherein said flexible sealing member is propped by said needle holder, and then said flexible sealing member is released from said inward flange to be automatically retracted into said plunger body due to a pressure.

2. The safety syringe according to claim 1, wherein said needle holder includes an outward flange, an external diameter of said outward flange is larger than a diameter of said needle holder.

3. The safety syringe according to claim 2, wherein said flexible sealing member includes a sealing rear portion and a holder-retaining front portion, said an external diameter of said sealing rear portion is larger than an internal diameter of said inward flange, said holder-retaining front portion is extended from said sealing rear portion and includes a blind hole, an internal diameter of said blind hole is smaller than said external diameter of said outward flange.

4. The safety syringe according to claim 3, wherein said flexible sealing member includes a curved projection.

5. The safety syringe according to claim 1, further comprising a rubber sealing ring sleeved around said plunger, wherein an external diameter of said rubber sealing ring is larger than said internal diameter of said syringe barrel.

6. The safety syringe according to claim 3, further comprising a piston body disposed within said blind hole.

7. The safety syringe according to claim 4, wherein said sealing rear portion includes a hollow space.

8. The safety syringe according to claim 1, wherein said needle unit includes a crook.

9. The safety syringe according to claim 8, wherein said flexible sealing member includes a sealing rear portion and an opening formed within said sealing rear portion.

10. The safety syringe according to claim 1, further comprising a U-shaped flexible element fastened by said flexible holder-supporting seat and said needle holder.

11. The safety syringe according to claim 10, wherein said U-shaped flexible element includes a hole penetrated by said needle.

12. The safety syringe according to claim 11, wherein said flexible sealing member includes a sealing rear portion.

13. The safety syringe according to claim 3, wherein a side in a front end of said inward flange expands and does not contact with said holder-retaining front portion.

14. A safety syringe, comprising:
a syringe barrel including a barrel body with a front opening, a rear opening, a front end wall and a rear end wall, wherein a cross-sectional area of said front opening is smaller than a cross-sectional area of said rear opening;
a flexible holder-supporting seat being disposed movably within said syringe barrel, wherein said flexible holder-supporting seat includes a central hole formed therethrough;
a needle unit including a needle holder, a crook and a needle penetrating said needle holder, said crook being disposed on a rear end of said needle holder, said needle unit is disposed movably within said front end wall, said needle holder being sleeved by said central hole of said flexible holder-supporting seat, wherein a rear opening is formed in said rear end of said needle holder, said needle is projected from said front opening;
a plunger including a front end with a front opening and an inward flange, a rear end and a plunger body formed between said front end and said rear end, a cross-sectional area of said front opening being larger than an external diameter of said needle holder, said plunger being disposed movably within said syringe barrel; and
a flexible sealing member sleeved by said inward flange to seal said front opening of said plunger, said flexible sealing member including an opening formed within said flexible sealing member to combine with said needle unit by said crook after said plunger being pushed to be close to said flexible holder-supporting seat, and then said needle unit being released from said flexible holder-supporting seat due to said plunger, wherein said flexible sealing member is propped by said needle holder, and then said flexible sealing member is released from said inward flange to be automatically retracted into said plunger body due to a pressure.

15. The safety syringe according to claim 11, further comprising a rubber sealing ring sleeved around said plunger, wherein an external diameter of said rubber sealing ring is larger than said internal diameter of said syringe barrel.

16. A safety syringe, comprising:
a syringe barrel including a barrel body with a front opening and a rear opening, wherein a cross-sectional area of said front opening is smaller than a cross-sectional area of said rear opening;
a flexible holder-supporting seat being disposed movably within said syringe barrel, wherein said flexible holder-supporting seat includes a central hole formed therethrough;
a needle unit including a needle holder and a needle penetrating said needle holder, said needle unit is disposed movably within said syringe barrel, said needle holder being sleeved by said central hole of said flexible holder-supporting seat, wherein said needle is projected from said front opening;
a U-shaped flexible element fastened by said flexible holder-supporting seat and said needle holder, wherein said U-shaped flexible element includes a hole penetrated by said needle;
a plunger including a front end with a front opening and an inward flange, a rear end and a plunger body formed between said front end and said rear end, a cross-sectional area of said front opening being smaller than an external diameter of said U-shaped flexible element, said plunger being disposed movably within said syringe barrel; and
a flexible sealing member sleeved by said inward flange to seal said front opening of said plunger, said flexible sealing member including a sealing rear portion to combine with said needle unit by injecting said needle into said sealing rear portion after said plunger being pushed to be close to said flexible holder-supporting seat, and then said needle unit being released from said flexible holder-supporting seat due to said plunger, wherein said flexible sealing member is propped by said needle holder, and then said flexible sealing member is released from said inward flange to be automatically retracted into said plunger body due to a pressure.

17. The safety syringe according to claim 16, further comprising a rubber sealing ring sleeved around said plunger, wherein an external diameter of said rubber sealing ring is larger than said internal diameter of said syringe barrel.

* * * * *